(12) United States Patent
Gupta et al.

(10) Patent No.: US 7,535,617 B2
(45) Date of Patent: May 19, 2009

(54) PORTABLE ACOUSTO-OPTICAL SPECTROMETERS

(75) Inventors: Neelam Gupta, Bethesda, MD (US); Vladislov I Pustovoit, Moscow (RU)

(73) Assignee: The United States of America as represented by the Secretary of the Army, Washington, DC (US)

( * ) Notice: Subject to any disclaimer, the term of this patent is extended or adjusted under 35 U.S.C. 154(b) by 223 days.

(21) Appl. No.: 11/208,123

(22) Filed: Aug. 18, 2005

(65) Prior Publication Data

US 2007/0041075 A1    Feb. 22, 2007

(51) Int. Cl.
*G02F 1/11* (2006.01)
*G02F 1/33* (2006.01)

(52) U.S. Cl. .................. 359/285; 359/287; 359/305; 359/308

(58) Field of Classification Search .......... 359/285, 359/287, 308, 311, 305, 298, 314
See application file for complete search history.

(56) References Cited

U.S. PATENT DOCUMENTS 4,582,397 A * 4/1986 Chang .................. 359/314

6,424,451 B1 * 7/2002 Chang .................. 359/308

* cited by examiner

*Primary Examiner*—Ricky L Mack
*Assistant Examiner*—Brandi N Thomas
(74) *Attorney, Agent, or Firm*—Paul S. Clohan; Guy M. Miller

(57) ABSTRACT

A portable acousto-optical (AO) spectrometer system comprised of at least one AO crystal cell device specially designed for cancellation of side-lobe noise at a desired tuned wavelength of operation. Each AO crystal cell device has a transducer attached and forms an AO tunable filter (AOTF) and forms part of a photo-head assembly. The system can include an optical fiber link between the AO spectrometer photo-head assembly and additional features such as an optical alignment coupling attachment that couple an excitation source such as a laser that operates in either pulse or continuous mode, a probing fiber that provides a hand-held member that can emit a source radiation and in turn observe radiation reflected from an observed sample. There are two embodiment of the AO crystal cell device. Either embodiment of the AO crystal cell design can be used in the system, providing a vibration-insensitive AO spectrometer instrument having high sensitivity, accuracy and resolution capabilities. The types of spectroscopic measurements that can be performed using the invention include fluorescence, Raman, absorption and emission.

8 Claims, 16 Drawing Sheets

ZONE 1

ZONE 2

PORTABLE ACOUSTO-OPTICAL SPECTROMETERS

BACKGROUND OF THE INVENTION

1. Field of the Invention

The invention relates in general to spectroscopy instruments for remote ultraviolet to infrared spectrum analysis and chemical analysis. More particularly, the invention relates to portable acousto-optical based spectrophotometers (spectrometers) for spectrum analysis, chemical analysis and of the species of interest.

2. Description of the Prior Art

Spectrometers are widely used for many applications such as chemical analysis, remote sensing, quality control, environmental monitoring, spaceborne measurements, and optical measurements. Most spectrometers are based on using dispersive elements such as prisms, gratings or etalons. These spectrometers typically have moving parts, which induce spurious readings due to vibrations, and have limited use due to their limited spectral range and resolution capabilities, which in turn limits their use when needed for portable field applications.

Acousto-Optical tunable filters (AOTF)s are very powerful tools that can be used in many spectroscopic applications, including absorption, emission, fluorescence, Raman, and laser-induced breakdown spectroscopy (LIBS) measurement instruments and inside of traditional, or fiber laser cavity for choosing and tuning frequency of light radiation. They are lightweight, compact, and very useful for field-portable applications. They have no moving parts, are all solid-state construction, require low power, and are insensitive to vibrations. They have high spectral resolution, large field of view and high throughput. They offer high-speed tuning and scanning of wavelengths and have reliable and reproducible operation under computer control. The wavelength tuning can be random or sequential, and an AOTF can be operated at multiple frequencies. AOTFs can be used for generating an arbitrary spectral response and can be used for polarization-sensitive applications. Such filters can be used as a replacement for filter wheels and gratings. Laser wavelength tuning applications use AOTF both inside and outside the laser cavity. AOTF spectrometers have been designed with both high sensitivity and high resolution. AOTF instruments are used for detection of chemical and biological agents and for medical and pharmaceutical applications, as well as for environmental sensing applications.

The AOTF is a birefringent crystal having an acoustic transducer bonded to one face. Broad-band light radiation passing through a crystal can be diffracted into specific wavelengths by application of a radio-frequency (rf) driving signal to the crystal transducer. The AOTF device can be used as a part of a spectrometer or other optical instrument. The AOTF has several advantages over alternative spectroscopic techniques such as filter wheels, diffraction gratings, and Fourier transform infrared. The AOTF crystal cell is small, fast, and reliable and has no moving parts. Because of these features, the AOTF crystal cell can be used for applications such as chemical process control, medical diagnostics, spectral radiometry, and real time composition analysis in the production environment. When coupled to fiber optics, the AOTF can be located remote from the sample of interest. This remote location has an advantage when the sample is in a harsh or potentially explosive environment. Fiber coupling reduces a chance of explosion by eliminating all electrical voltage in the sampling region. Among the attractive features of AOTFs are their small size, light-weight, computer-controlled operation, large wavelength tuning range, and reasonably high spectral resolution. Additionally, their operation can be made ultrasensitive by using advanced signal-processing algorithm.

The AO effect allowed for the development of an AOTF, which was not discovered until much later in 1967, when a new type of AO interaction was discovered in anisotropic crystals (in such crystals the speed of light with different vector of polarization is different). Two years later this AO effect was used in a collinear AOTF cell using lithium niobate ($LiNbO_3$) and successfully demonstrated. In a collinear AOTF, the incident light, the acoustic wave, and the diffracted beam all travel in the same direction. A number of different crystals, i.e., quartz, $LiNbO_3$, etc., allow collinear diffraction of light with either longitudinal or shear acoustic wave propagation. Chang generalized the design of an AOTF cell by introducing the concept of a noncollinear AOTF using tellurium dioxide ($TeO_2$), a birefringent crystal (a crystal having two refractive indices) that cannot exhibit collinear interaction because of its crystal symmetry. In a noncollinear AOTF cell the incident light, the diffracted light, and the acoustic wave do not travel in the same direction. At present, a number of AOTF cells and AOS's are available commercially and as research instruments. The United States, Russia, and Japan are the leading players in this technology. Since the first commercial offering of AOTF by the Isomat Corporation in 1975, this technology has made much progress. Near-IR (900-1800 nm) AOS are now commercially available.

An AOTF is essentially a real-time programmable filter whose operation can be described as follows. When white light is incident on the filter, it passes only a selected number of narrow bands corresponding to the applied rf-signals. The filter can be used to pass light with either a single wavelength or multiple wavelengths, depending upon the number of applied rf-signals. Either a collinear or a non-collinear geometry can be used in designing an AOTF cell, based on the symmetry properties of the anisotropic crystal under consideration. The incident light is linearly polarized by a polarizer in front of the crystal before it enters the AOTF cell. As this polarized light passes through the cell, it is diffracted in the same direction by a diffraction grating set up by the collinearly traveling sound wave. Owing to conservation of energy, the frequency of the diffracted light is Doppler shifted, but this frequency shift is insignificant and can be ignored. Based on conservation of momentum, a tuning relationship can establish between the center wavelength of the filter and the applied rf-signal. Many excellent review articles on AOTF technology and applications are available, for example see Gottlieb, M. S., "Acousto-optic tunable filter," *Design and Fabrication of Acousto-Optic Devices*, A. P. Goutzoulis and D. R. Pape, eds., Marcel Dekker, New York, 1994, pp. 197-283; Gupta, N., ed., Proceedings of the First Army Research Laboratory Acousto-Optic Tunable Filter Workshop, Army Research Laboratory, ARL-SR-54 (1997); and Gupta, N. and Fell, N. F., Jr., "A compact collinear Raman spectrometer," *Talanta* 45, 279-284 (1997).

An example of a spectrometer using AO crystal cells includes U.S. Pat. No. 5,120,961 entitled "High sensitivity acousto-optic tunable filter spectrometer," which teaches of using an acousto-optical filter (AOTF) device in a spectrometer. This spectrometer operates by using continuous wave RF-excitation through the crystal, wherein the spectrometer provides control and modulation of the RF-source. Noise is minimized by a lock-in amplifier that demodulates the modulation frequency. Fiber optics are used to connect the crystal to the source, and the source to the detection system. In contrast, the present invention preferably uses pulsed-wave RF-excitation through the crystal(s) for control of the AO crystal cell.

An ongoing problem in using spectrometers in more applications is their miniaturization. The size of a spectrometer is limited by their required precision and accuracy of measurements because of existing relationships between optical spectral resolution, spectral range of a spectrometer and its inherent physical dimensions. The optical spectral resolution of commonly manufactured spectrometers is proportional to their dimensions. This is a noted and important limitation for miniaturization of spectrometers, which heretofore generally cannot be circumvented. Unfortunately, since precise spectrometers for use in environmental analysis are often bulky, costly, and expensive to transport and install, many known and important applications of spectrometers remain unimplemented due to cost and/or inconvenience.

In particular, miniaturization of equipment for Raman spectroscopy applications is a current problem. Raman spectroscopy is a powerful analytical technique that provides complete identification of chemical agents based on their electronic vibrational energy levels. This technique is typically confined to controlled laboratory environments because Raman signals are very small and require very high sensitivity, high-resolution spectrometers with special attachments to do these measurements. Also, highly trained personnel are needed to setup and run these experiments. Fluorescence measurements are used to detect biological particles. AO-type spectrometers used in Raman spectroscopic measurements, generally require high sensitivity and resolution. Previously known such spectrometers include a collinear acousto-optic spectrometer called a "Quartz 4," which was constructed in the former Soviet Union and made of quartz. This instrument provided measurements in the visible light spectral range of 430-800 nm and less sensitive compared to the instant inventions AO spectrometer subassembly provided herein due to the crystal design. Additionally, known Raman and fluorescence spectroscopic systems are generally large, cumbersome, hard to maintain, take much time to setup, and operate over limited spectral ranges. For applications that require field portability, these systems cannot generally be used. Also, most currently used spectroscopic systems cannot be used to take both Raman and fluorescence spectral measurements simultaneously because each of these measurement techniques has different system requirements. Most of these current systems have moving parts such as gratings, filter wheels, or moving mirrors for tuning at a desired optical wavelength.

Thus, there is a need for a portable AOTF spectrometer system that is relatively less expensive compared to currently available systems that can be produced and packaged for field hand-held use by non-experts. Thus, the present invention addresses these problems by providing an autonomous, integrated spectrum-measurement-based spectroscopy system for UV-Vis-IR spectral ranges of interest, and a system that can be adapted for Raman and fluorescence spectral measurements as well.

SUMMARY AND ADVANTAGES OF THE INVENTION

The invention relates to a field portable acousto-optical (AO) spectrometer system comprised of at least one AO crystal cell device specially designed for cancellation of side-lobe noise at a desired tuned wavelength of operation. Each AO crystal cell device has a transducer attached and forms an AO tunable filter (AOTF) that in turn forms part of a photo-head assembly. The system can include an optical fiber link between the AO spectrometer photo-head assembly and additional features such as an optical alignment coupling attachment that is coupled to a source such as a laser that can be operated in either pulse mode or continuous mode, a probing fiber that provides a hand-held member that can emit a source radiation and in turn observe radiation reflected from an observed sample.

A first embodiment of the acousto-optical (AO) crystal cell device comprises a cut birefringent AO crystal cell made of quartz. The cut has a special shape so that all unwanted sound waves are absorbed after traveling through an AO interaction region. An incident initial light beam passes through a polarizer such that the light entering the AO crystal cell is linearly polarized. The rf-signal applied to the crystal through a transducer attached at the lower side of the crystal produces sound waves that first propagate upward and subsequently get reflected from a cut facet of the crystal. These sound waves propagate until absorbed within the crystal. Diffraction of light takes place in the entire AO interaction region due to the nonlinear parametric coupling of sound and light waves caused by a photo-elastic effect in the crystal cell material. The diffracted beam has a polarization orthogonal to the incident polarization. The diffracted beam plus the non-diffracted portion of the incident beam pass through another polarizer that separates the diffracted beam, which is focused on a photo-multiplier (PMT) detector of the observed signal. The spectro-photometer system when using this embodiment of the invention includes computer/controller hardware that generates a signal pulse that is applied to the crystal cell, the computer processor also senses the PMT signal and contros rf-signals to a transducer attached to the crystal cell. The single AO crystal cell can be used in combination with other systems that have non-spectroscopic applications.

A second embodiment of the acousto-optical (AO) cell device comprises two AO crystals that can also be part of the AO spectrometer photo-head assembly. Each crystal has an attached transducer and positioned with respect to each other so as to provide an in-line single diffracted beam from unpolarized incident radiation. Lenses can be used when a collimated beam is used. Rf-signals having equal power and same frequency are applied to these two transducers. Between the two crystal cells, an optical aperture occurs that lets only collimated diffracted light from the first crystal pass through it. The undiffracted portion of the incident beam is blocked by this optical aperture. Next the diffracted beam with polarization goes through a second diffraction when transmitted through the second AO whose orientation is opposite to that of the first crystal. The second crystal diffracts the incident collimated beam such that polarization of the doubly diffracted beam in a single plane. Thereafter, the beam goes through a second optical aperture that blocks the undiffracted beam from the second crystal focused on a detector using a lens. See color picture FIG. 5C. When this embodiment is used in a spectrophotometer system, the measured signal goes to the computer/controller hardware for processing and output of useful measured data. This double crystal cell can be used in other non-spectroscopic AOTF applications as well.

Either embodiment of the AO crystal cell design can be used in the portable, vibration-insensitive AO spectrometer instruments having high sensitivity, accuracy and resolution capabilities. These AO spectrometer (AOS) cell designs are based on anisotropic Bragg diffraction in a birefringent crystal, i.e., quartz, lithium niobate, tellurium dioxide ($TeO_2$). The fundamental building block of an AO spectrometer systems is application of electronically tunable filters. Such systems can operate in spectral ranges from 255-800 nm when using quartz crystals and from 400-4500 nm when using $TeO_2$ crystals. Either embodiment of the AO crystal cell designs can be used in spectroscopic systems used for fluorescence, Raman, absorption and emission-type spectral measurements.

Applications of the invention include, but not limited to detection of infectious diseases, cancer, toxic agents, drug interdiction, airport security, spaceborne environmental monitoring, detection of forest fires, underwater monitoring of gases, diagnostics of engines using condition-based management of engine oil, and water quality monitoring, and for fiber optic laser and telecommunication.

Accordingly, advantages of the present invention include providing an acousto-optical spectrophotometer system that is:

(a) capable of greater spectral range capabilities and is much more sensitive and accurate compared to presently used conventional diffraction grating based spectrometers;

(b) portable and inexpensive to produce that can be used in fluorescence, Raman, emission, and absorption spectrometer systems;

(c) inclusive of a non-collinear double crystal AO cell that has relatively high signal to-noise-ratio due to suppression of energy in side lobes of the diffracted beam at a desired tuned wavelength, thereby enabling systems in which it is incorporated to have greater accuracy, resolution and sensitivity;

(d) inclusive of a single collinear AO crystal cell design with a special cut facet that has relatively high signal to-noise-ratio due to suppression of energy in side lobes of the diffracted beam at a desired tuned wavelength, thereby enabling systems in which it is incorporated to have greater accuracy, resolution and sensitivity; and (e) that allows for portable field use of both Raman and fluorescence type measurements by non-experts.

Still further advantages will become apparent from consideration of the ensuing detailed description of the preferred embodiments.

BRIEF DESCRIPTION OF THE DRAWING

FIG. 6b shows the methodology for making spectroscopic measurements shown in FIG. 6a;

In the drawings and constituted as such, like numerals indicate like parts.

DETAILED DESCRIPTION OF THE PREFERRED EMBODIMENT

Figure 1:
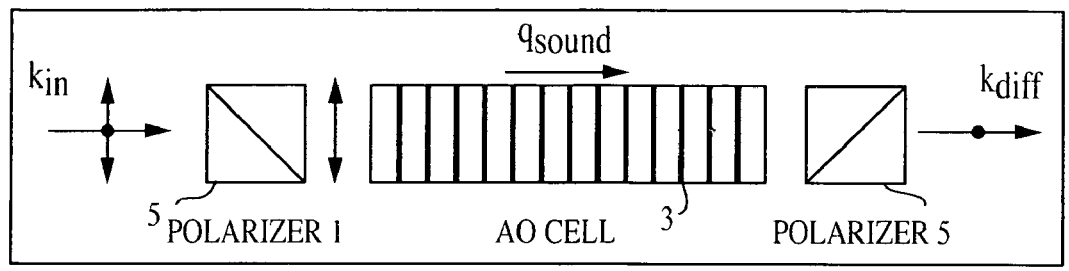
FIG. 1 shows a schematic layout of a collinear AOTF cell used in AO spectrometer devices.
Figure 2:
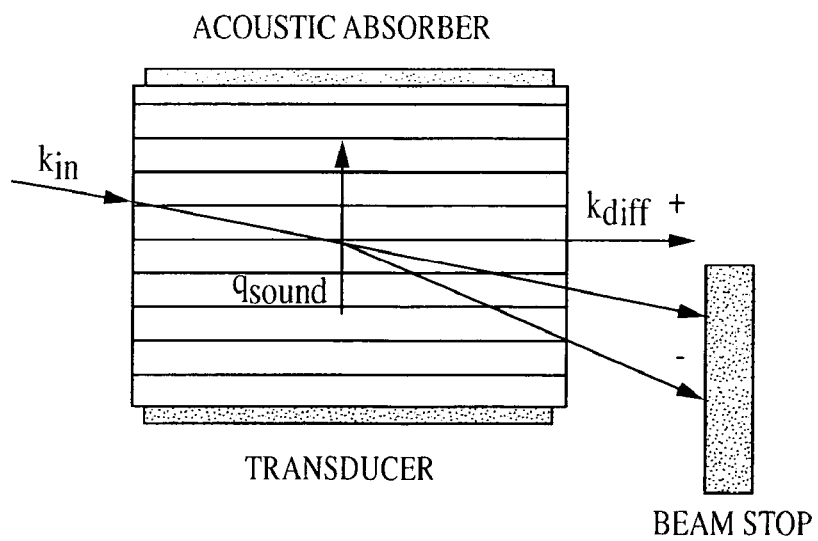
FIG. 2 shows a side-view of a non-collinear AOTF cell used in AO spectrometer devices.

AOTF Concepts: There are two types of AOTF cells: collinear and non-collinear as shown in FIGS. 1 and 2 respectively. FIG. 1 shows the propagation of light and sound in a collinear AOTF cell. The wave vectors for the incident and diffracted light are $k_{in}$ and $k_{diff}$ respectively, and for sound wave it is $q_{sound}$. The incident light is linearly polarized by a polarizer in front of the crystal medium of interaction. As polarized light passes through the crystal perpendicular to the optic axis, it is diffracted in the same direction by a sound wave traveling collinear to the incident optical beam. Since the polarization of the diffracted beam is perpendicular to the incident light beam, it can be separated from the incident beam with the use of an analyzer. Due to the conservation of energy, the frequency of the diffracted light is Doppler shifted. Because the frequency of the incident light is around $10^{14}$ Hz and the frequency of the ultrasonic beam is around $10^8$ Hz, the Doppler frequency shift is insignificant and can be ignored. Based on the conservation of momentum, a tuning relationship between the center wavelength of the filter and the applied rf frequency can be established:

$$i.\ k_{dif} = k_{in} + q, \quad (1)$$

$$\lambda = (n_o - n_e) v_s / \Omega \quad (2)$$

where $k_{dif} = 2\pi n_o / \lambda$ ... $\square$ is the center wavelength of the filter, $n_o$ and $n_e$ are the refractive indices of the crystal corresponding to the propagation of light along the ordinary and extraordinary polarization of light, respectively, and $v_s$ and $\square$ are the speed and frequency of the acoustic wave, respectively. The AOTF bandwidth is equal to $\lambda^2/\Delta nL$, where L is the length of the AO interaction (same as the length of the crystal), and $\Delta n$ is the difference of the two refractive indices.

FIG. 2 shows a schematic layout of a non-collinear AOTF cell. Here the diffracted beam is spatially separated from the un-diffracted beam. This may look like a regular Bragg cell, but due to the anisotropic nature of the AO interaction involved, the polarization of the diffracted beam is orthogonal to that of the incident beam, and each of these beams travels with a different speed in the crystal.

In acousto-optical spectrometer (AOS), the AOTF cell must first be selected for the application having a desired spectral range of operation. The crystal needs to be cut with a specific orientation and polished. Next, a transducer (such as LiNbO3) is bonded to the crystal using Indium. The traveling acoustic wave is generated in this crystal by applying an rf-signal to the transducer. The tuning range for a single transducer is about one octave in acoustic (and optical) frequency; however, an AOTF cell can be designed with multiple transducers to cover a wider frequency range of operation. Also, it is very important to grow many intermediate thin layers of various materials (Sn, Ag, Au, etc.) for proper acoustic matching of the sound wave with the crystal surface over the entire rf-range to ensure that most of the acoustic signal is transmitted through the crystal and does not get reflected back. Once the acoustic signal traverses the cell, it is absorbed by an acoustic absorber on the opposite side of the crystal.

The performance of an AOS is primarily limited by the quality of materials used. For an interaction medium of an AOTF, this material must be optically birefringent and transparent in the operating wavelength range of desired use. Also, it must have a low acoustic attenuation in the acoustic frequency range of operation, low depolarization properties so the material must minimize crystalline domains within the material. Also the material must possess a large AO figure of merit. Table 1 lists a number of important crystal materials, their spectral ranges of coverage and type of cell that can be fabricated.

Materials for Designing AOTF Cells

TABLE 1

| Material | Spectral band ($\mu$m) | Type of cell |
| --- | --- | --- |
| Crystal Quartz | 0.25-0.8 | Both |
| LiNbO3 | 0.4-4.5 | Collinear |
| CaMoO4 | 0.4-4.5 | Collinear |
| TeO2 | 0.35-4.5 | Non-collinear |
| Tl3AsSe3 (TAS) | 1.3-17 | Both |
| Hg2Cl2 | 0.35-20 | Non-collinear |
| Hg2Br2 | 0.35-30 | Non-collinear |

After selection of an AOTF cell type, an electronic circuit operates the cell and transducer(s) attached to the crystal cell(s). The electronic circuit includes a rf-signal generator, a wide-band rf-amplifier to amplify the applied preferred pulsed rf-signal; and a power supply for the detector, where the electronic circuit is controlled by a central processing unit (computer with multiple ASSIC boards for required signal generation and control). This output signal from the detector is then processed by a computer and be analyzed using signatures of known compositions by comparison therewith. Advanced signal processing algorithms can be incorporated in the software of the CPU as well to control operation of the AO crystal cell devices and provide many output data processing functions for a particular application. An example of such electronic control circuitry is taught in U.S. Pat. No. 5,120,961, as discussed above and incorporated by reference, but contrast with the present invention which uses pulsed RF-signals applied to the transducers that are attached to the AO crystal cells.

AO Spectrometer Crystal Cell Devices:

One way to improve AOS performance is amplitude modulating the sound waves within the crystal with a period so that selection of two states of controlled acousto-optic filtering can occur; the first state being when a sound wave is absent and only parasitic components caused by the spurious aspects are present, and the other being when a sound wave incident and useful signals plus the parasitic component are present. Given that during modulation of the sound wave, radiation intensity does not change, subtracting the photocurrent value observed during the first state from the value observed during the second state, a resultant yields a value proportional only to a useful, diffracted portion of the radiation. Thus, significant signal quality improvement is obtained.

Measurement accuracy of a spectral radiation distribution of light using acousto-optic spectrometers is the main task. Most current AO spectrometers inherently measure spurious outside signals of a desired band of spectral measurement when using an acousto-optic filter and then received by a photodetector. This spurious radiation creates a bias level in an observed signal, apart from noise component, which contains some value proportional to intensity of the band of observed radiation. Physical reasons which lead to "squeezing through" of this spurious radiation can be caused by less than desirable optical system components that are used in the spectrometer apparatus, low quality of crystals used in the AOTF (for example, considerable depolarizing properties or occasional optical activity), low contrast of polarizers, bad quality of optical surfaces, on which there occurs radiation scattering with the change of polarization, and input radiation diffraction on optical waves reflected or scattered in the crystal itself.

These factors lead to decreased measurement accuracy of spectral energy intensity, which must be minimized and/or compensated for. To reduce the impact caused by these factors by amplitude modulation of sound waves within the crystal having a standard period so that two states of controlled acousto-optic filtering occurs: one being when a sound wave is absent and then measuring only parasitic components, caused by radiation passing through the optical components of the apparatus, and the second being when a sound wave is present and measuring useful signals plus the initial parasitic component. Given that during modulation of the RF-signal, radiation intensity has not changed and subtracting the bias-noise signal from a detected signal, a resulting value proportional only to diffracted portion of radiation can be obtained. By using this amplitude modulation and signal subtraction concept, a decrease in error connected with defects of optical system can be obtained. However, parasitic signals caused by diffraction of sound waves reflected from a crystal's boundary have not been accounted for. To reduce this factor on measurement accuracy, a special geometry of interaction between light and sound is provided by the invention herein so that reflected waves do not interact with input excitation radiation directed at a sample. This problem is resolved as discussed below using sound wave phase modulation comprising sound wave phase modulation in a certain period using a step function. This changes a synchronous interaction length between light and sound waves within a crystal and consequently the amplitude of diffracted radiation emanating from the crystal. These changes happen with a period multiple to run time of phase shift region on crystal length and that is why with the help of methods of synchronous detection there can be picked out only signal diffracted on the main sound wave, as light diffraction on reflected sound waves occur with some time delay.

Besides these problems, there are physical ones connected with the diffraction process itself. In fact, functioning of an AO spectrometer system, generally has the form:

$$h(\Delta k) = \frac{\operatorname{Sin}^2\left[\Gamma L\sqrt{1+\left(\frac{\Delta k}{2\Gamma}\right)^2}\right]}{1+\left(\frac{\Delta k}{2\Gamma}\right)^2} \quad (3)$$

where $\Delta k = k_{in} - k_{dif} - q_s$ is a wavevector mismatch, i.e., deviation of wave vector from the value satisfying a condition of synchronism. $\Delta k = k_{in} - k_o$, where $$k_o = \frac{\Omega}{v_s |n_o - n_e|}$$

is the value of the wave vector satisfying condition of synchronism. $\Omega$ is the sound frequency, L is an interaction length between light and sound wave.

$$\Gamma = \frac{p(n_o n_e)^{3/2} \pi^2 P_{ac}^{1/2}}{\lambda \sqrt{2\rho v_s^3}}$$

is the coefficient of acousto-optic interaction, defining acousto-optic properties of crystal. For example for longitudinal sound wave propagation in x-direction, non zero component of the deformation tensor will be $S_{xx} \neq 0$, or in the alternate six-digit notation system, $S_1 \neq 0$, (direction x corresponds to direction 1) and change in the dielectric tensor will be $\Delta \epsilon_{23} = \Delta \epsilon_{32} = n_o^2 n_e^2 p_{14} S_1$, where $p_{14} \equiv p$ is the corresponding photo-elastic constant and $S_1 \equiv S$ is elastic deformation caused by the acoustic wave in crystal, and $P_{ac}$ is the elastic energy density, $P_{ac} = \rho v_s^3 S^2$, where $\rho$ is density and $v_s$ is the velocity of sound in the crystal.

From formula (3) it can be seen that the maximum transparency of AOTF will be when $$\Gamma L = \frac{\pi}{2},$$

or in other words there exists an optimal value of the elastic energy density, $P_{ac}^{opt}$, which can fulfill the conditional $$\Gamma L = \frac{\pi}{2},$$

i.e., $$\Gamma = \frac{p(n_o n_e)^{3/2} \pi (P_{ac}^{opt})^{1/2}}{\lambda \sqrt{2\rho v_s^3}} L = \frac{\pi}{2}.$$

Using this definition of $P_{ac}^{opt}$, formula (3) can be rewritten as $$h(\Delta k) = \frac{\operatorname{Sin}^2\left[\frac{\pi}{2}\eta\sqrt{1+\left(\frac{\Delta k}{2\Gamma}\right)^2}\right]}{1+\left(\frac{\Delta k}{2\Gamma}\right)^2},$$

Where $$\eta \equiv \left(\frac{P_{ac}}{P_{ac}^{opt}}\right)^{\frac{1}{2}}.$$

Using this expression for $h(\Delta k)$, it is convenient to write formula (3) in the following form:

$$h(\eta, \xi) = \frac{\operatorname{Sin}^2\left[\frac{\pi}{2}\eta\sqrt{1+\frac{N^2}{\eta^2}\left(\frac{1-\xi}{\xi}\right)^2}\right]}{1+\frac{N^2}{\eta^2}\left(\frac{1-\xi}{\xi}\right)^2}, \quad (4)$$

where $N = 2L/\Lambda$ is the number of semi-waves of sound wave with wavelength $$\Lambda = \frac{2\pi v_s}{\Omega},$$

in the interaction length, $\xi = \lambda/\lambda_0$, is the ratio of wavelength of light $\lambda$ to wavelength $\lambda_0$ corresponding to realization of condition of synchronism when there is maximum transparency and sound power. As a result of light diffraction from sound wave, energy of diffracted radiation will be unevenly spread in the spectrum: maximum intensity will be in the region of "transparency window" of AOS, but a certain portion of diffracted radiation will not fully conform to formula (4) over the full spectral range. (Here, it is assumed that initial radiation is evenly spread over the full spectral range.) Formula (4) gives the transmit function of AOTF as a function of $\xi$. This formula is more convenient in carrying out digital calculations.

Let us take a ratio of light energy which is concentrated inside the transparency window, i.e., inside the throughput band of AOS, with energy in the remaining portion of spectral distribution. For this a throughput band is defined for the acousto-optic spectrometer as a half distance between two nearest minima of formula (4), which is
given by $$\Delta k = 2\Gamma \sqrt{\frac{4m^2}{\eta^2} - 1} \ldots \square.\tilde{}$$

where $m = 1, 2, 3, \ldots$ is a minimum integer value fulfilling condition $(2m/\eta) > 1$. Alternately, using the signs of formula (4) for relative values of wavelengths of AOS band, we can define a distance between minima as $$\xi^+ - \xi^- \cong \frac{2}{N}[4-\eta^2]^{1/2} \ldots \text{for } m = 1, .\square^\sim \neq .\eta \ldots \square.$$

where $\xi^+$ and $\xi^-$ are two neighboring minima near main maximum of $h(\eta,\xi)$, i.e., $$\xi^+ = \frac{N}{N - \sqrt{4m^2 - \eta^2}},$$

$$\xi^- = \frac{N}{N + \sqrt{4m^2 - \eta^2}}.$$

This result is a corollary of formula (4).

It is clear from formulas (3) and (4), that considerable portions of energy can be present outside of the throughput band, in the side "transparency windows," also known as side-lobes of a sinc function, which is inherent in the energy distribution. Accounting for the energy in these "transparency windows" for a particular spectral distribution of observed radiation in an acousto-optic spectrometer can significantly improve detection accuracy of such instruments.

Assuming that the spectral distribution of measured source of radiation is a wideband even distribution, i.e., at each wavelength radiation intensity is same and conventionally it is set equal to one. A ratio is defined by evaluating the amount of energy contained inside the "transparency window" of an ideal spectrometer with the corresponding portion of energy contained in the remainder of the optical range, as follows.

$$\zeta(P) = \int_{\xi^-}^{\xi^+} h(\eta, \xi) d\xi \bigg/ \left( \int_{\xi_{min}}^{\xi_{max}} h(\eta, \xi) d\xi - \int_{\xi^-}^{\xi^+} h(\eta, \xi) d\xi \right) \quad (7)$$

where $$\xi_{max} = \frac{\lambda_{max}}{\lambda_0},$$

and $$\xi_{min} = \frac{\lambda_{min}}{\lambda_0}$$

are dimensionless values of wavelengths corresponding to measured spectral band $\{\lambda_{min}, \lambda_{min}\}$.

Figure 3:
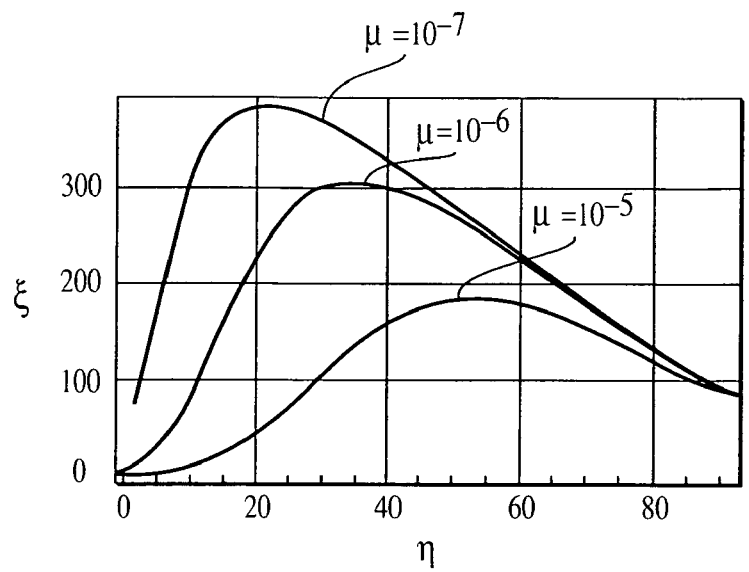
FIG. 3 shows a graph of ratio of energy of diffracted light in the main maximum to the energy in whole spectral interval for a two-crystal cell design of an AOS depending on P for the three different levels of parasitic signals mu ($\mu$) labeled on the corresponding curves.
Figure 3A:
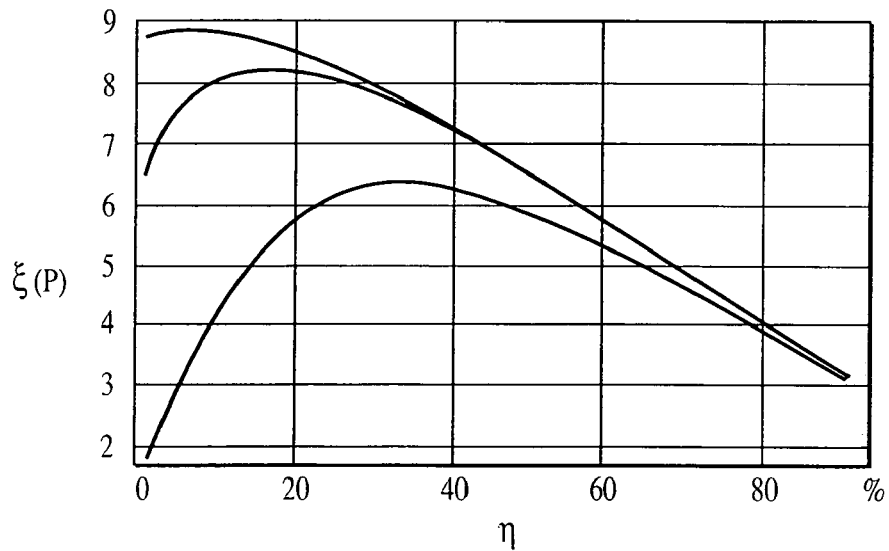
FIG. 3a shows a graph of ratio of energy in the transparency window of an AO filter to side-lobe energy as sound wave intensity P is increased for one-crystal AO monochromator for different level of parasitic signal: $\mu=10^{-7}$ (upper curve), $\mu=10^{-6}$ (middle curve), and $\mu=10^{-5}$ (lower curve).

From formula (7), this ratio depends on the product ΓL, and hence the intensity of sound wave η. It can be shown from this formula that if there is an increase in energy of sound waves in the transparency window then energy in the remaining region of spectrum sharply decreases. This is unexpected due to the fact that with an increase of sound wave intensity, the diffraction of radiation in the region outside the conditions of synchronism increases at a greater rate compared to intensity of the desired main maximum radiation, and the relative portion of energy inside the main maximum decreases monotonously (that is, to increase accuracy and reliability of a measured result, a decrease in sound wave intensity in the crystal must occur, but the value itself to which such decrease is possible, is defined by the level of parasitic incident radiation). In view of equation (6), this can be written as:

$$\zeta(P) = \int_{\xi^-}^{\xi^+} h(\eta, \xi) d\xi \bigg/ \left( \int_{\xi_{min}}^{\xi_{max}} h(\eta, \xi) d\xi - \int_{\xi^-}^{\xi^+} h(\eta, \xi) d\xi + \mu \right) \quad (8)$$

where μ is the level of parasitic signal that can be considered independent of wavelength. The ratio of the "transparency window" to side lobe energy according to equation (7) is shown in FIG. 3a. Thus, for each level of parasitic signal μ, there is a certain level of sound wave intensity at which detection capacity becomes largest. (Detection capacity is defined as a ratio of energy portion of diffracted radiation in the main maximum lobe of the radiation energy profile at desired wavelength to energy, concentrated in the whole spectral interval outside of the main maximum. It is assumed here that spectral distribution of measured radiation source is even).

In a two-crystal AO cell optical design, when light is diffracted in one cell, it is transmitted to the second cell where repeated diffraction occurs. If both AO cells are the same and in each there are excited sound waves of equal intensity, and their frequencies are equal, then AOTF device with double crystal design $h_D(\eta,\xi)$ can be written as:

$$h_D(\eta,\xi) = h^2(\eta,\xi). \quad (9)$$

As discussed above, a ratio of energy of diffracted radiation in the main peak of AOS to energy in the rest of the entire optical range for the case of double-crystal spectrometer design is given by $$\zeta_D(\eta) = \int_{\xi^-}^{\xi^+} h^2(\eta, \xi) d\xi \bigg/ \left( \int_{\xi_{min}}^{\xi_{max}} h^2(\eta, \xi) d\xi - \int_{\xi^-}^{\xi^+} h^2(\eta, \xi) d\xi \right) \quad (10)$$

Using above equation (10) in computations, and comparing the detection capacity of a double-crystal AOS to a single crystal AO spectrometer device, we find it to be considerably greater. In the case of a single-crystal scheme, there exists some value of sound wave intensity at which detection capacity is the largest. However, the detection capacity for a double-crystal scheme is considerably higher then for a single-crystal.

Figure 3B:
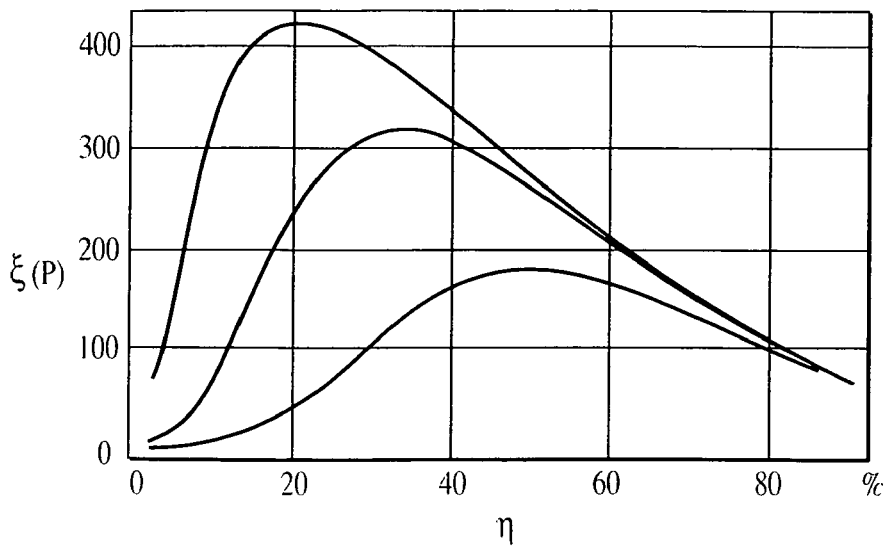
FIG. 3b shows a graph of a ratio of energy of diffracted radiation in the main maximum to energy in the whole spectral interval for a two-crystal cell design (upper curve) and a one-crystal cell design (lower curve) of an AOS depending on P for the level of parasitic signal: $\mu=10^{-7}$ (upper curve), $\mu=10^{-6}$ (middle curve), $\mu=10^{-5}$ (lower curve).

FIG. 3b shows from equation (10) a graph of a ratio of energy of diffracted radiation in the main maximum to energy in the entire spectral interval for an AO two-crystal cell design.

Figure 4E:
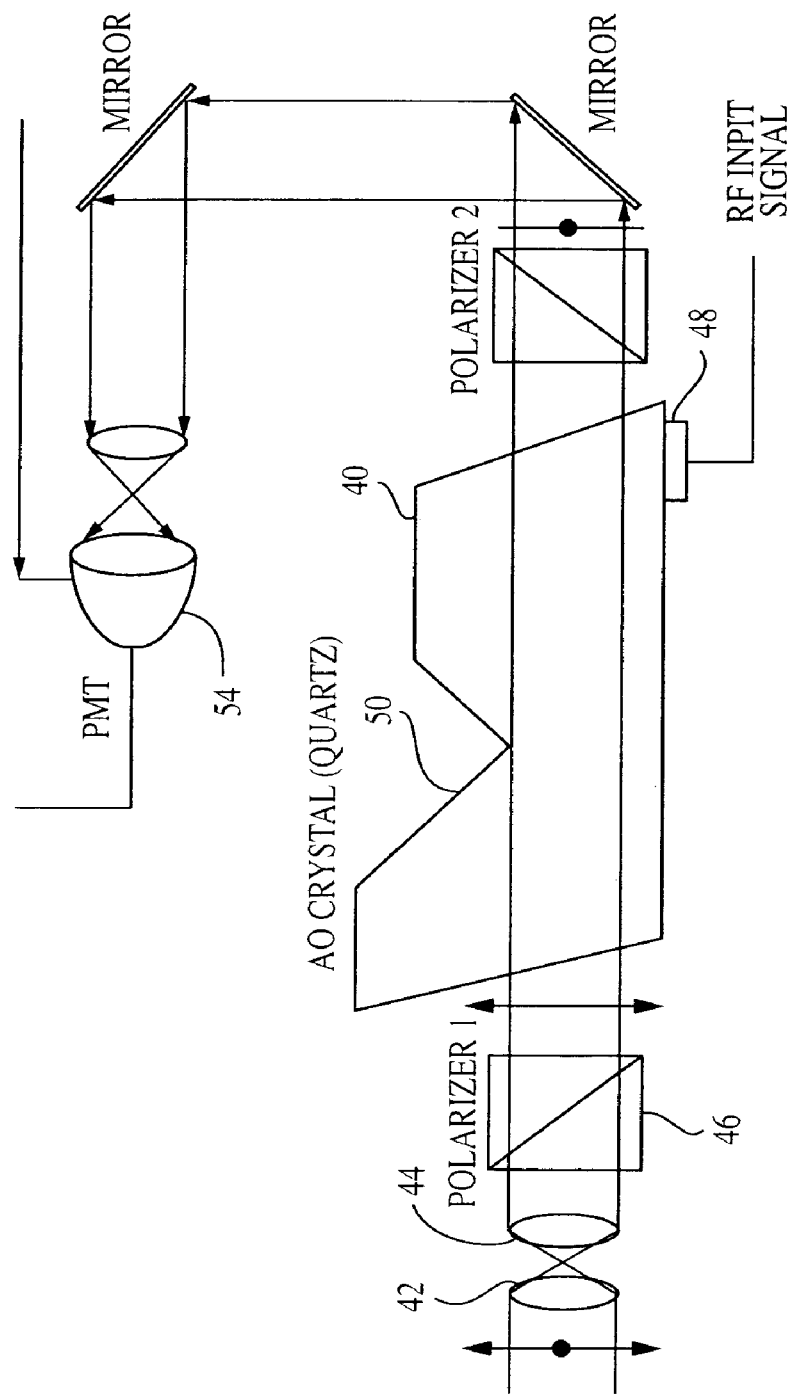
FIG. 4e shows principle optical scheme: photo-head with collinear AO cell (FIG. 4b, FIG. 4c).
Figure 5A:
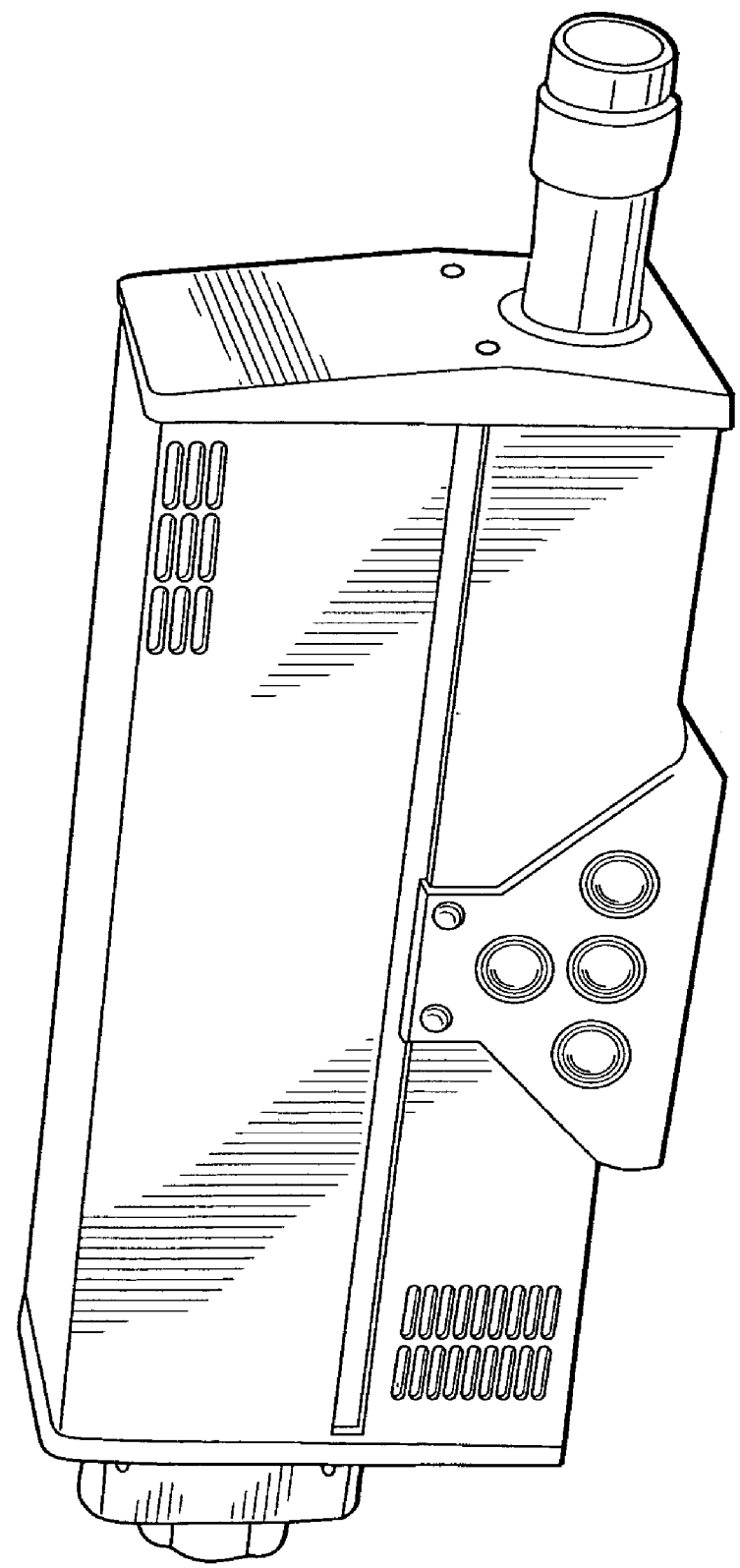
FIG. 5a shows a side-view of a second photo-head assembly using a non-collinear AOTF device.

Non-collinear Double AO Crystal Cell Device: FIG. 5a shows a first photo-head embodiment of an acousto-optical (AO) device 100A used in spectrometer apparatus 1000 as photo-head assembly 100 in FIG. 4e.

Figure 5B:
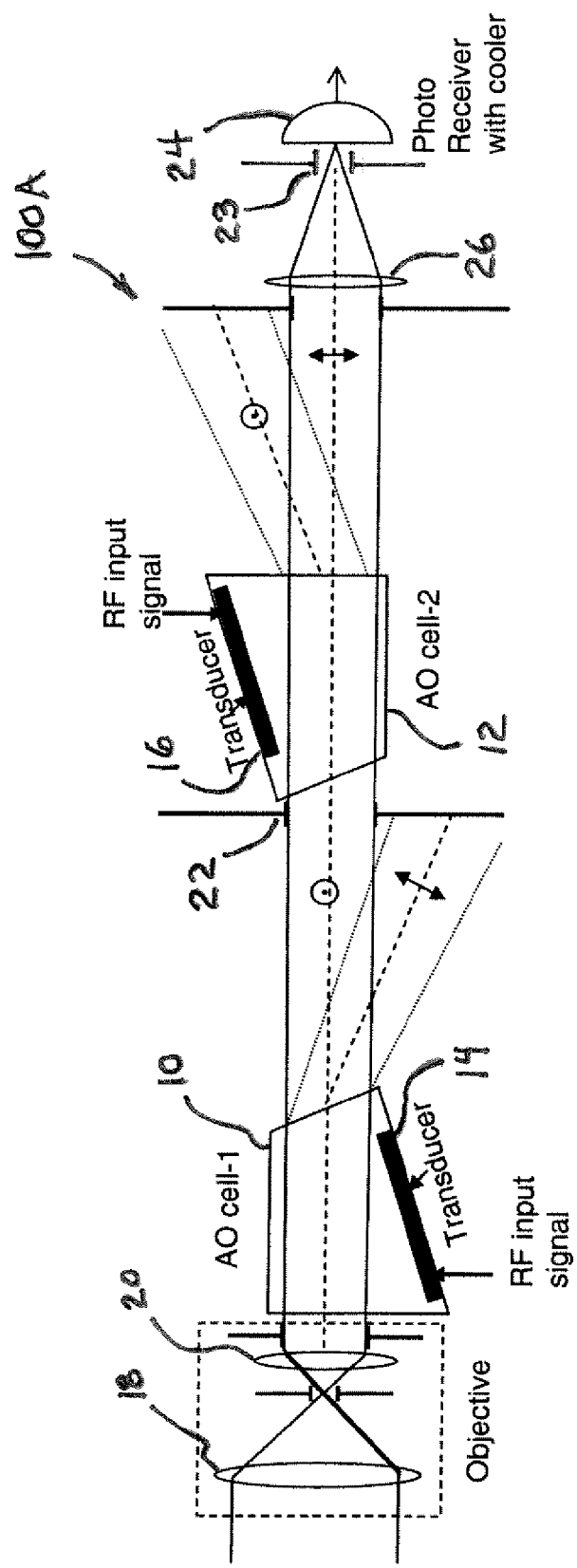
FIG. 5b shows principle optical scheme: photo head with double-crystal monochromator.
Figure 5C:
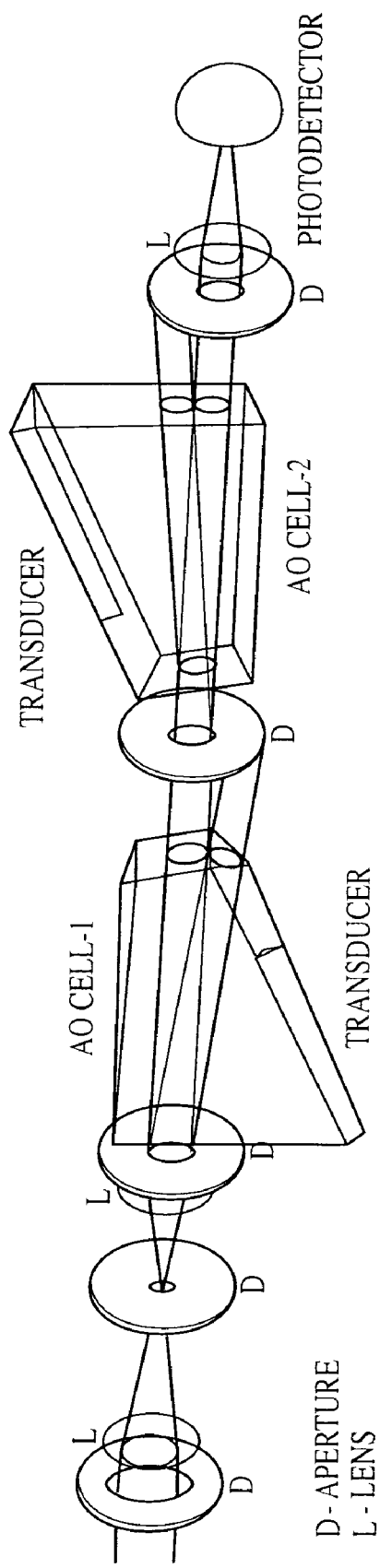
FIG. 5c shows 3-D optical scheme, which are shown in FIG. 5b (D-Aperture, L-lens).
Figure 6A:
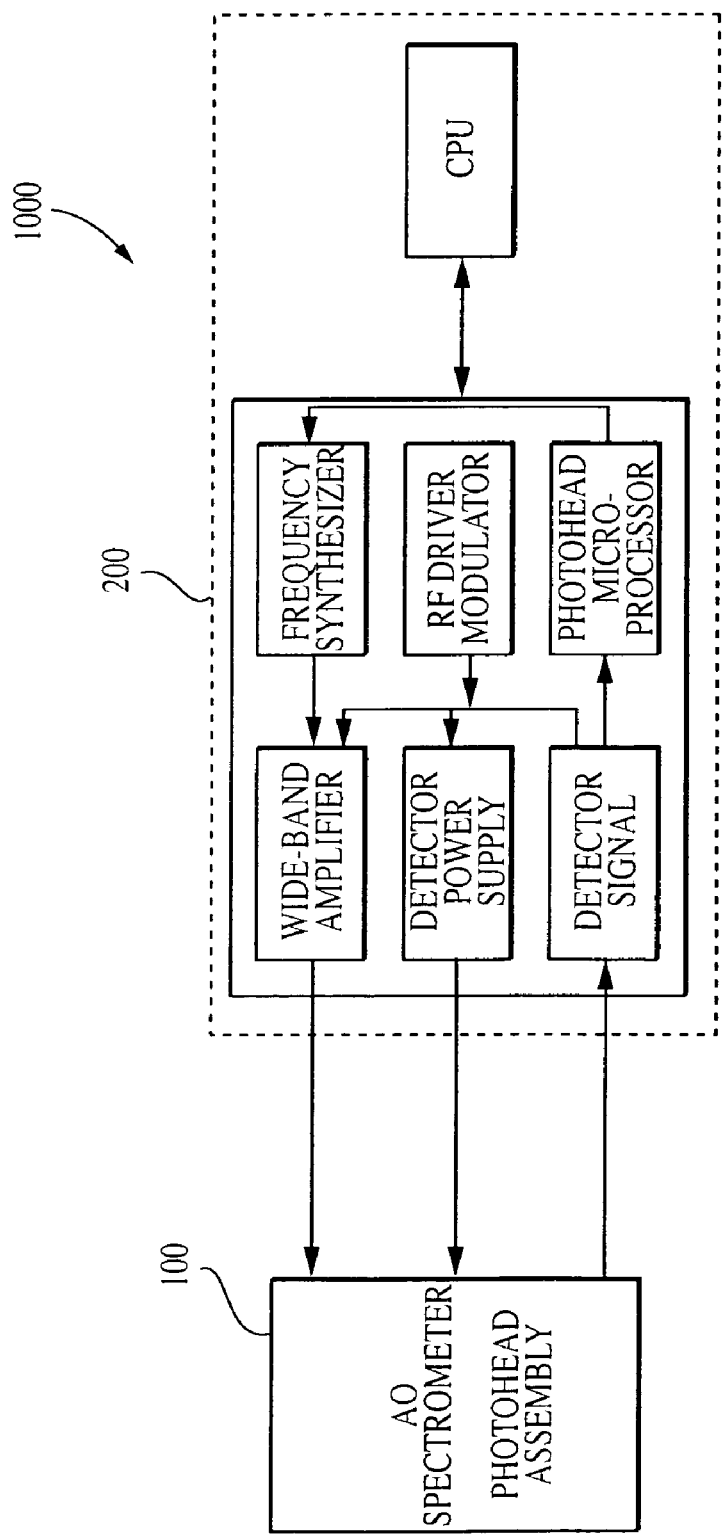
FIG. 6a shows a block diagram of several-major components of a portable AO spectrometer system.

In FIGS. 5b and 5c, the AOTF device 100A comprises two AO crystal cells 10 and 12 with transducers 14 and 16 that are positioned in such a way as to provide an in-line single diffracted beam from the un-polarized incident collimated white light beam coming through a combination of two beam forming lenses 18 and 20. The rf-signals of approximately equal power and same frequency are applied to each of the transducers 14 and 16 on the two AO crystals 10 and 12. Between the two crystals, an optical aperture 22 is located so as to let only the collimated diffracted light from the first crystal 10 pass through it. The un-diffracted beam is blocked by optical aperture 22. Next, this diffracted light beam with polarization normal to the plane of the figure goes through a second diffraction from the second AO crystal 12 with transducers whose orientation is opposite of the first crystal and crystal 12 diffracts the light such that the polarization of the doubly diffracted beam is parallel to the plane of the FIG. 5b and perpendicular to 5b the direction of light propagation. This beam again goes through a second optical aperture blocking the un-diffracted beam from the second crystal 12. The diffracted light is now focused on a detector 24 using a lens 26. The measured signal by the detector 24 goes to the central processing unit (CPU) as shown in FIG. 6a for processing and output display of useful information.

The AO double crystal device 100A is based on principles of inhomogeneous Bragg diffraction using a non-collinear geometry, wherein beams of incident light, sound and resultant diffracted light beams do not travel in the same direction. The crystals are birefringent crystals made of either $TeO_2$ (tellurium dioxide), TAS (thallium arsenic selenide) or mercurous halides. The spectral band of operation depends upon the transmission region of the crystal medium (for $TeO_2$, the spectral band of transmission is from about 0.35 to 4.5 micrometers; for TAS, from about between 1.3 and 16 micrometers; for mercurous chloride, from about between 0.35 to 20 micrometers, for mercurous bromide from between about 0.35 to 30 micrometers; and for mercurous iodide, from between about 0.45 to 40 micrometers) and upon the design of the transducers 14 and 16 (that typically have a single octave in frequency capability), but using a combination of transducers as well as newer designs of transducers can extend this range for much greater coverage. This can be done by proper acoustic impedance matching between the transducer(s) that are attached to a crystal at the bonding layer.

The double crystal geometry provides an in-line diffracted beam by using a special cut of the crystal such that one of the diffracted beams has much greater intensity than the other one. These crystals are preferably two specially oriented thin sheets of lithium-niobate that are connected electrically in series. Each crystal cell 10 and 12 has a wedge structure that provides correction for color blurring caused by angular spread of different wavelengths of light. The orientation of each of the crystals with respect to each other is symmetrical so that corresponding surfaces are parallel to each other, see FIG. 5c. As discussed above, the relative orientation of the two crystals 10 and 12 is selected so as to reduce the side lobes in the diffracted beam at a desired tuned wavelength of operation by more than 30-times compared to using a single crystal alone, and intensity loss due to the second crystal 12 is less than 30% and spectral resolution increases 50% when using the second crystal. The detection sensitivity of the AO device 100A depends on the sensitivity of detector 24 that detects the diffracted light beam. By using a cooled detector, much greater sensitivity can be achieved compared to when using an un-cooled detector.

A preferred optical design of the AO device 100A uses non-polarized radiation formed by telescopic object-glass lens 18 and 20 having a focus distance of 44 mm and 17.5 mm respectively. Each lens is made of fluorite, a material that is transparent in an IR range. The two identical AO cells are made of $TeO_2$ crystals are preferably located in a beam path such that diffraction occurs in the AO cell 10 and radiation is transmitted to the second AO cell 12. The non-diffracted portion of radiation is cut-off by apertures 22 and 24. Diffracted radiation is then focused by lens 26 and detected by a detector 24 (a cooled photo-receiver). When using AO devices using a LiNbO3 transducer 14, longitudinal sound waves are reflected from a crystal cell's boundary, which are transformed into transverse sound waves. This embodiment of an AO design can be used in non-spectroscopic applications that include AOTF components.

Figure 5D:
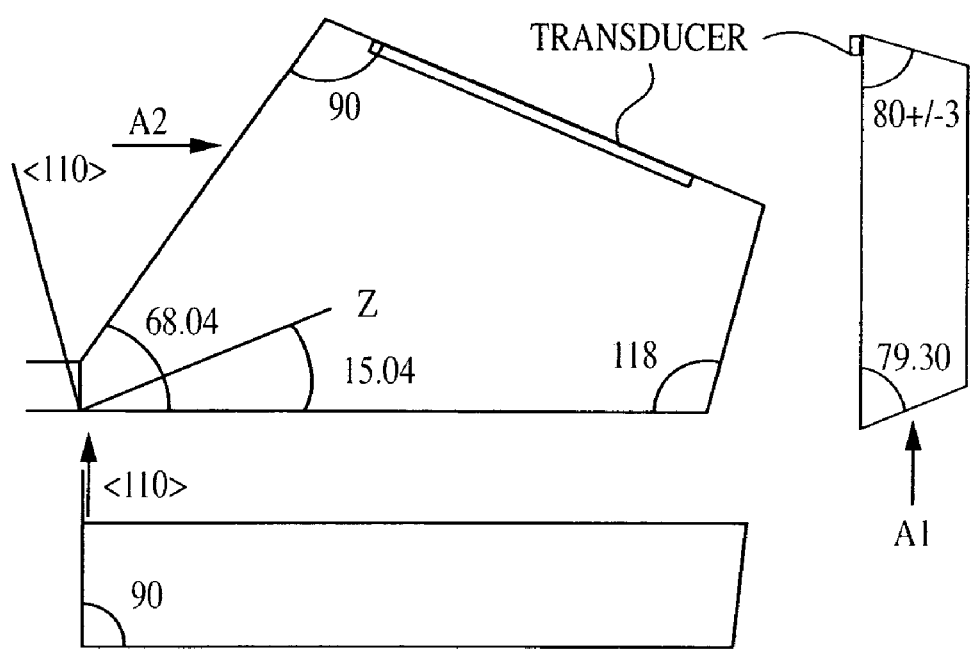
FIG. 5d shows space orientation and main angles of non-collinear AO cell from $TeO_2$ (3 different projections).
Figure 5E:
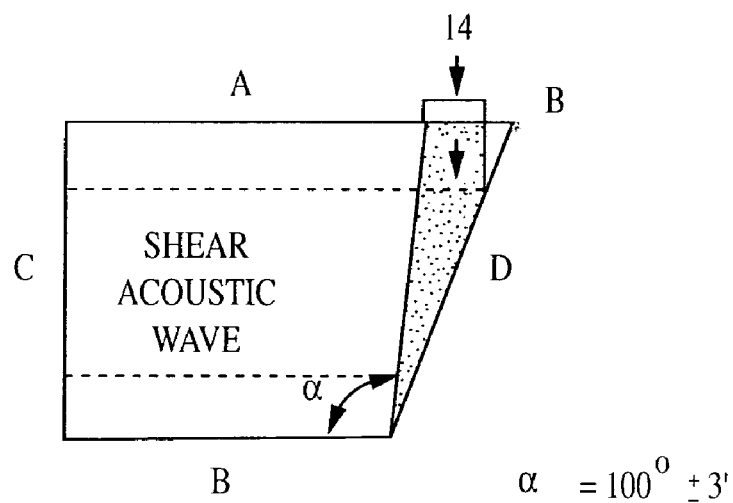
FIG. 5e shows a partial view of the AO cell of FIG. 5d depicting the interaction regions within the cell.

FIG. 5d shows in exemplary form of one of the AO cells 10 and 12 using this embodiment of the AO cell design. The crystal has top, bottom, left and right faces, A, B, C and D, respectively, see FIG. 5e. Top face A and Bottom face B are parallel to one another. Left face C is perpendicular to top and bottom faces A and D. Right face D is shown oriented at an angle (a with respect to face B. AO cell from $TeO_2$ has rather complex configuration, which is shown in FIG. 5d for three mutual orthogonal projections. In FIG. 5d main angles of this AO cell are shown as well as the specified orientation of crystal axis with respect to edges of AO cell (for 2-5 microns spectral band $TeO_2$ AO cell). Angle □ is determined based on the crystal properties such that an acoustic wave traveling in a direction normal to the face of side A will result in a shear acoustic wave reflected off of face D propagating in a direction normal to faces A and D. The transducer 14 is positioned on face A such that the acoustic wave $K_{in}$ reflects off of the middle of face D. The most important parameters in designing a non-collinear AOTF cell are the angle of incidence of light and the AO interaction length. Cell design is made by use of optimizing equations for a field of view of the AOTF cell and diffraction efficiency for a given crystalline material and requisite operational spectral resolution of the AOTF. The angle alpha for a particular material is obtained using this optimization procedure.

Preferably when making the AO cells 10 and 12, identical AO cells 10 and 12 are used for respective pairs of cells as part of the AO device 100A by making both cells from the same crystal, which is cut into two halves. Coatings (Rose alloy) for sound wave absorption are applied to appropriate surfaces using ultrasonic spraying. The transducers 12 and 14, typically $LiNbO_3$ plates having appropriate orientation for acoustic wave excitation of the AO cells. Initially, these transducers are made by applying a chrome layer to each of the crystal cells by vacuum spraying, followed by an aluminum layer on which electrodes are attached. Silver-coated copper film is used as electrodes. They are attached using ultra-sonic soldering-iron and Rose alloy. A thin layer of indium is attached to aluminum. Next, LiNbo3 plates are welded to this layer. Next, they are polished to achieve proper thickness (so that plate's thickness is approximately ½ of the inducing sound wavelength). A silicon oxide layer is then sprayed over, which protects each of the transducers from electrical discharge. Next, a layer of aluminum, to which another electrode is attached. A typical cell 10 and 12, has a spectral range is 1.1-2.7 microns (or 2-5 microns), spectral resolution is 2.5 nm at 1.15 microns, spectral position precision of +/−2.5 nm, and an acoustic frequency range of 35-77 MHz.

Shaped Collinear AO Crystal Cell Device: A second embodiment of an AO device 100B is shown in FIGS. 4a and 4b, 4c and 4d, which alternatively can be used in spectrometer apparatus 1000 as the photo-head assembly 100 in FIG. 6a.

A birefringent AO crystal cell 40, preferably made of quartz, is cut in a special shape such that all unwanted sound waves are absorbed after traveling through an AO interaction region. The incident light beam may optionally pass through a pair of lenses 42 and 44 see FIG. 4e to form a collimated beam with diameter equal to approximately 10 mm, next the collimated beam passes through a polarizer 46 such that the light entering the AO crystal 40 is linearly polarized. An rf-signal applied to the crystal 40 through a transducer 48 attached to a side of the crystal produces sound waves, which initially propagate through and subsequently reflected from the cut facets of the crystal until absorbed at a boundary A, B, and C of the cut facets at a mid-section of the crystal. The facets 50 are cut in such a way as to not let sound wave get reflected into the crystal and retrace its original path in the AO interaction region. The diffraction of light takes place in the entire region of AO interaction due to the nonlinear parametric coupling of sound and light waves due to a photo-elastic effect in this crystal material. The conservation of momentum condition requires that for a given applied rf-signal, only one wavelength of light with a narrow band-pass can be diffracted. A diffracted beam has a polarization orthogonal to the incident polarization. The diffracted beam plus the non-diffracted portion of the incident beam pass through another polarizer that separates the diffracted beam, which is focused on a photo-multiplier (PMT) detector 54 that detects the observed signal.

Figure 4A:
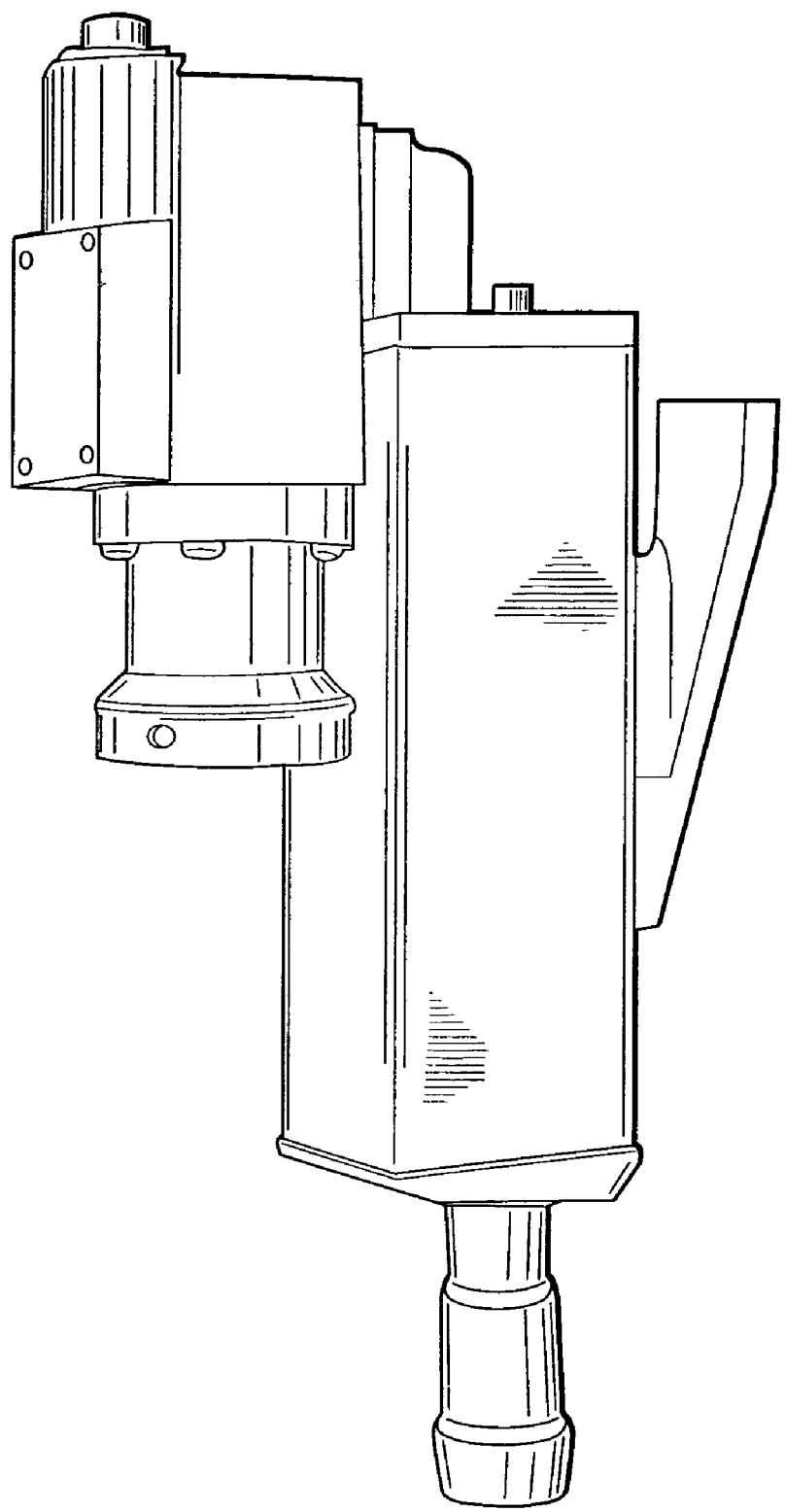
FIG. 4a shows a side-view of a first embodiment of a photo-head assembly for use with portable spectrometers, using a collinear AOTF device.
Figure 4B:
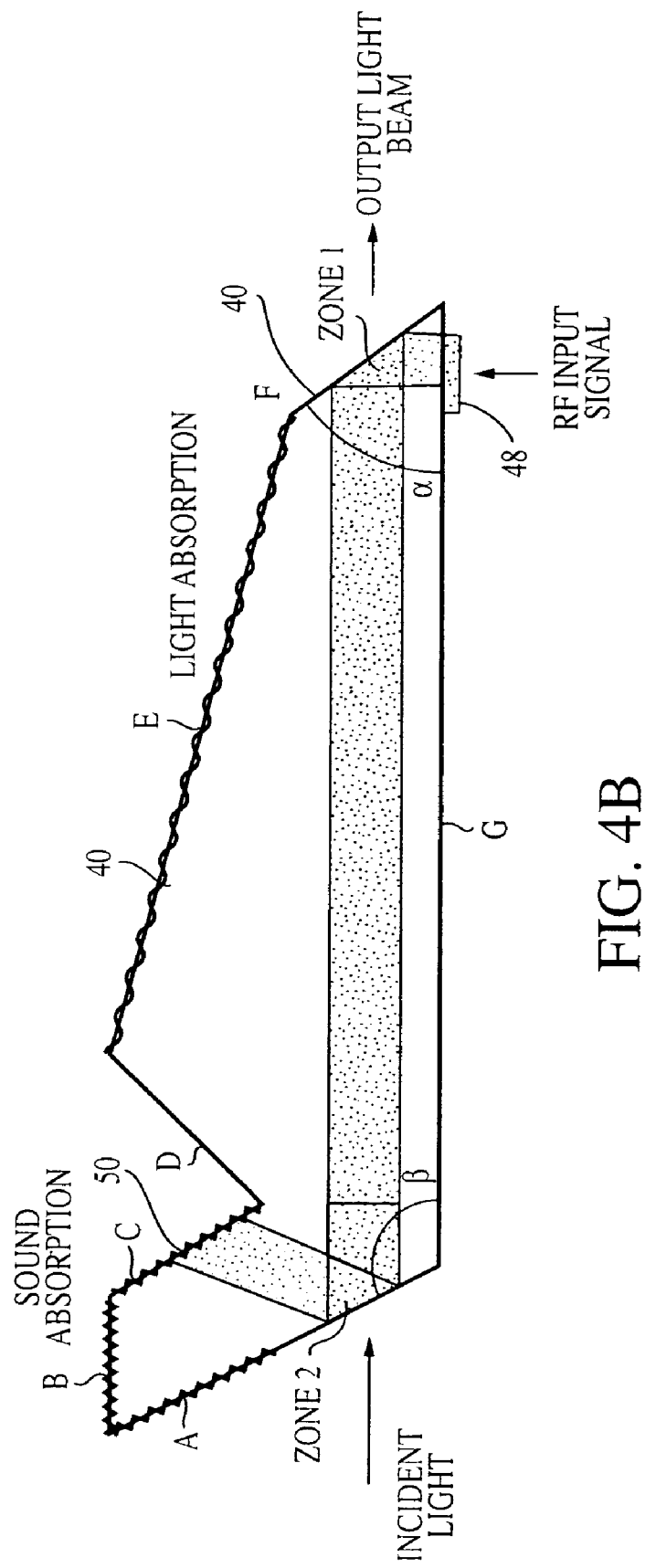
FIG. 4b shows collinear AO cell configuration of sound and light propagation and main angles.
Figure 4C:
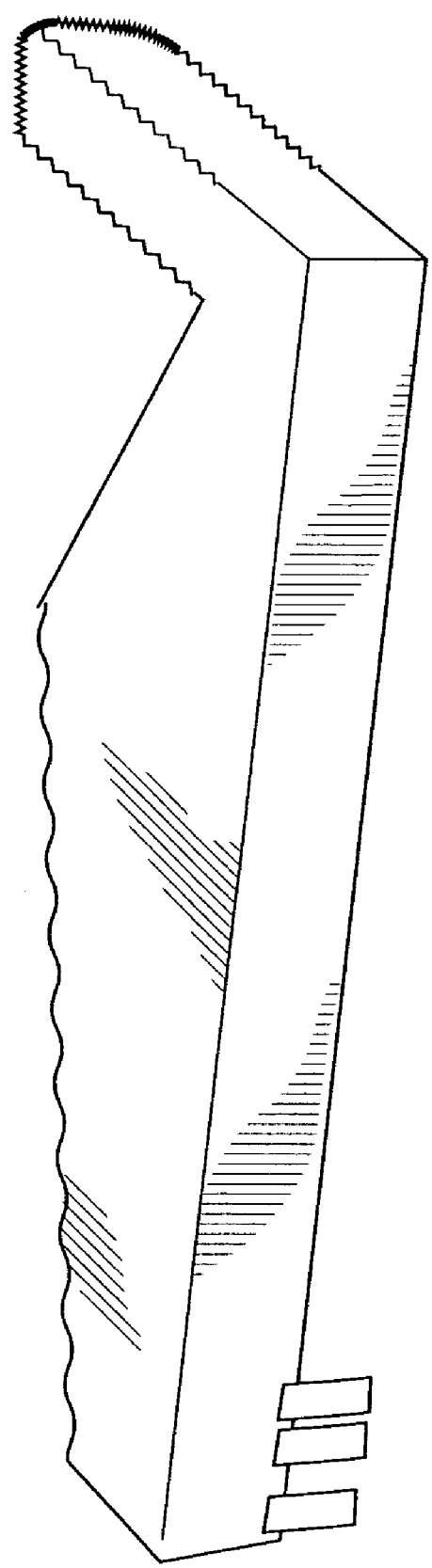
FIG. 4c shows a side-view of collinear AO cell using in AO devices.
Figure 4D:
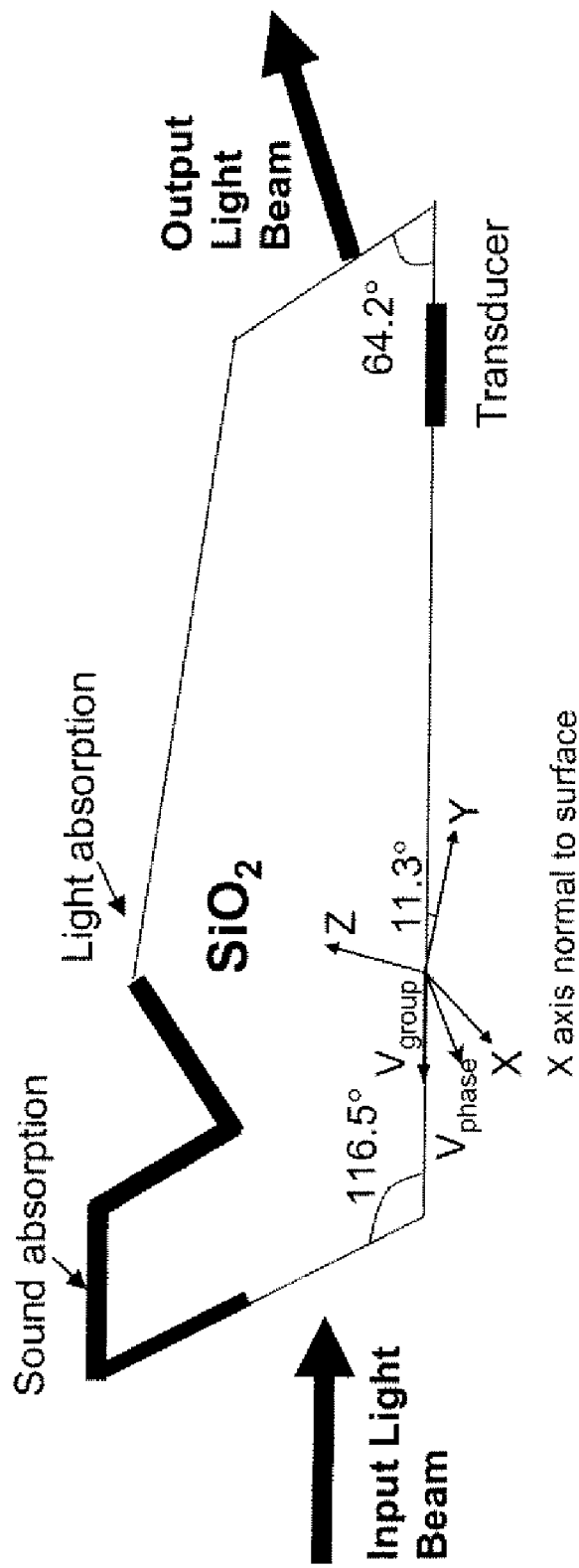
FIG. 4d shows collinear AO cell and mutual orientation of crystal axes with respect to surface of AO cell.

FIG. 4*b* shows details of the interaction AO regions within the cell of an exemplary birefringent AO crystal 40, which is preferably made of quartz, cut in a special shape such that all unwanted sound waves are absorbed after traveling through an AO interaction region. Crystal 40 has 7 faces, A, B, C, D, E, F and G. An rf-signal is applied to transducer 48, which in turn produces sound waves, which initially propagate through and subsequently reflected from cut facets of the crystal until absorbed at boundary B of the cut facets. The facets 50 and A are cut in such a way as to not let sound wave get reflected into the crystal and retrace its original path in the AO interaction region. The same part of face A also cover absorption material (see real picture of FIG. 4*c*). As shown, a typical quartz crystal 40 has a UV-spectral band (225 nm-430 nm) wherein the input light polarization is horizontal. When using quartz as the cell material, representative angles for cut facets: $\alpha$ is approximately 64 degrees and $\beta$ are approximately 116.5 degrees. These angles are representative and differ when another crystalline material is used.

Figure 5F:
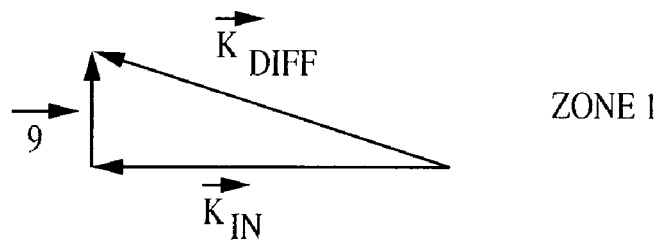
FIG. 5f shows a vector diagram of a tuning relationship between the center wavelength of a filter and the applied rf-frequency using AO cell of FIG. 5a in a first zone.
Figure 5G:
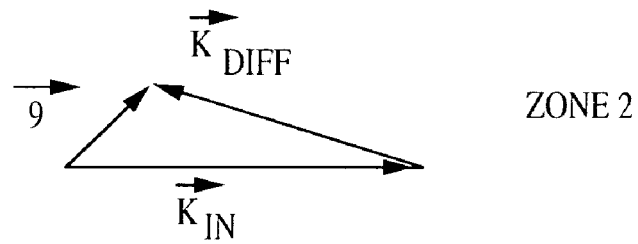
FIG. 5g shows a vector diagram of a tuning relationship between the center wavelength of a filter and the applied rf-frequency using AO cell of FIG. 5d in the second zone.

FIG. 5*f* and FIG. 5*g* show vector diagrams of the tuning relationship between the center wavelength of the AO filter and the applied rf-frequency of FIG. 5*f* in zones 1 and 2 respectively. These regions are where sound travels in a direction across the path of the polarized incident light beam. Sound absorption occurs at surfaces B after reflection from surface A. Light absorption of diffracted radiation occurs at regions D and E from zones 1 and 2.

FIG. 6*a* shows the electronics portion of an exemplary spectrometer apparatus 1000 using either an AO photo-head devices 100A or 100B. There are three interconnections between the AO device 100 and the electronics section 200 of the apparatus. One connection applies the rf-signal to the transducer(s) attached to the AO device from a wide-band amplifier. Another transmits power to the detector and a third connection senses a detected signal from the detector for signal processing by the CPU. The rf-driver, frequency synthesizer, wide-band amplifier, and the detector signal are preferably contained within a unitary computer tower structure. A measured output signal from the detector is processed by the CPU and powered by standard signal voltages of ±12 V and ±5 VDC. The AO device 100 is controlled by the computer and appropriate control software. Such software can be C++ language.

Figure 6B:
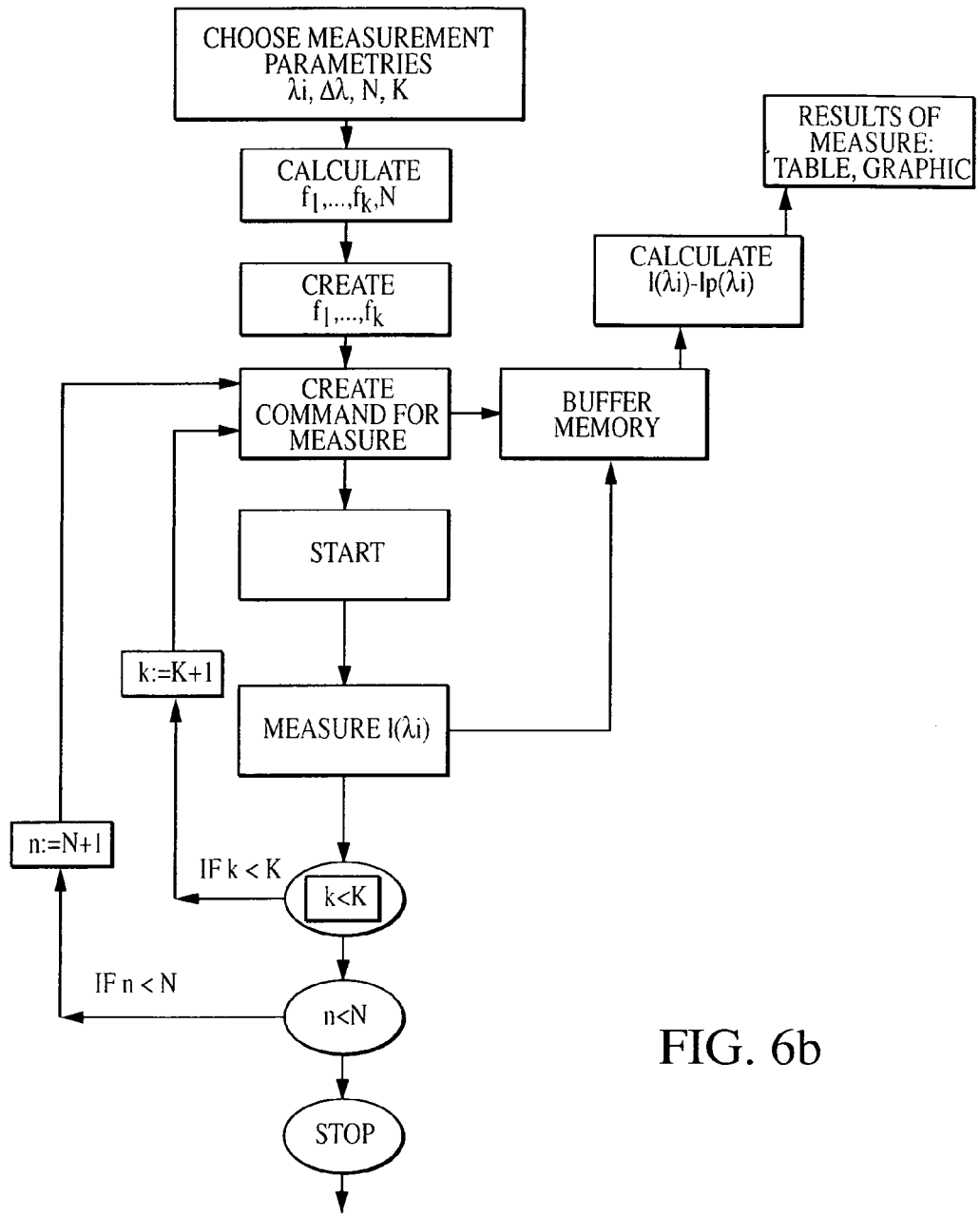

FIG. 6*b* shows in block diagram form the methodology for making measurements and controlled by the computer/controller 200. The control of the frequency synthesizer within is determined by desired spectral band of measurement and a value of measured spectral resolution. Additionally, a command for controlling the modulation of the rf-driver amplifier is incorporated. The photocurrents measured by the AO spectrometer photo-head assembly 100 are conditioned and digitized. The computer/controller 200 also incorporates data transmission protocols for use with a user friendly interface for inputting and outputting information from the system 1000 and controls operational conditions such as monitoring temperature of the AO crystal cells, voltage to the rf-driver modulator, the amplifier, and the photo-detector unit.

The flow diagram shown in FIG. 6*b* is defined as follows: n is current run number on the spectrum; K is a given number of runs; f0 is an initial value of frequency; fK is an endpoint of frequency; fk=f0−k'□f defined as an interim frequency spot; N is a number of accumulations, and Ip(□i) is measured parasite signal.

Preferably, each AO cell of the AOS device 100 are transparent birefringent crystal(s) having lithium niobate piezoelectric transducer(s) bonded to surfaces of the cells as discussed above. The detectors may be any device, which responds to the magnitude of the optical intensity and optical wavelength received from a target sample under observation. A typical detector sensitive to the infrared wavelength range from 1 to 6 microns is a lead selenide detector. If the radiation is in the visible range, a silicon photodiode may be used for the detector. Still further, a lead sulfide, germanium, or various types of detectors may be used for other wavelengths. The output of the detector could be any electronic signal or parameter change due to the changes of receiving optical intensity and wavelength, for example a voltage, a current, a resistance or a capacitance change. The choice of parameter change is dependent upon the type of detector used. For instance, a lead selenide detector produces an impedance change response. The detectors may also incorporate a cooler, which is useful for noise reduction that includes thermal noise, excess noise and dark current noise. A current source may be used to supply bias current to the detector if required. Photovaristor detectors need bias voltage sources, or current sources, but photovoltaic detectors do not need any additional bias support. The wide-band amplifier is a low noise amplifier, which amplifies the signal and converts the signal to a voltage output from detector. If the signal output is voltage, then the preamplifier may be a typical amplifier, which directly amplifies the voltage. On the other hand, if the output from detector is an impedance change signal, then the preamplifier must convert the signal to a voltage signal, and provide a voltage output. The CPU input is a digital signal, which is proportional to the magnitude of the demodulated AC signal detected by detector. The detector ideally is a very fast detector, which can respond to frequencies in the order of several megahertz. For a counting regime, this must be more than 100 megahertz. In some cases, a lead sulfide detector can be used since it is relatively slow. The CPU processes the signals and controls the RF frequency synthesizer in the system. The CPU generates a display, which provides either quantitative or qualitative measure. The CPU may also produce a qualitative analysis. In the qualitative analysis, the spectrum is scanned, and the spectrum of transmission, absorption or corresponding data according to wavelength displayed. The CPU may also be used to identify unknown samples. A computer program may have a spectrum library, which stores the information regarding the spectral characteristics of various elements or chemical compounds. The computer will then compare the spectral information received from an unknown sample with spectral patterns retained in the library, and identification of unknown sample can be made by comparison. The CPU can also control the RF frequency applied to the AOS device 100.

The RF-driver signal to each crystal cell using either embodiment of the AOS device is determined by a microprocessor that is separate and apart from the main CPU of the apparatus 1000. This microprocessor with own clock signal, which controls the transmitted RF signal to each crystal, is a function of required spectral resolution, a minimum and maximum frequency of a tuned frequency for the cell, temperature of the AO crystal cells, power level of the RF signal, value of a required power level for certain detector devices. As an example, a PMT transducer can be at one of 4-power levels and any one of these power levels has a bearing upon the control of the output RF signals to the crystal. The acquired data signal is governed by this microprocessor that uses real-time data acquisition techniques. In particular, a periodic sampling period occurs wherein during a portion of initial on-portion of the sample period, T1, a sample is taken to acquire an observed event and ambient bias level. Next during sample-off portion T2, a bias level is determined. Finally during a sample portion T3, the signal S(T1)-S(T2) determines a desired measured signal. Multiple samples can be taken and stochastic methods are used to interpret the data. The period of measurement can be varied for required use.

There are two spectrometer designs, which cover the range from UV to near IR using the computer tower structure and optical assembly 100 described above. These two optical assemblies that can operate from 255-430 nm and the other from 400-800 nm run from the same controller with menu driven choices in the software. The specifications of these two spectrometers are listed in Table 2. Each spectrometer typically weighs several pounds and can be packaged in an envelope of approximately 10 inches long, 4 inches in height, and 1.5 inches wide. Table 2 that follows has specifications for a UV, Vis-NIR, and Mid IR AOS Devices as follows:

TABLE 2

| Parameters | UV | Vis-NIR | Mid-IR |
|---|---|---|---|
| Cell material | Quartz | Quartz | TeO2 |
| Cell type | Collinear | Collinear | Noncollinear |
| Spectral range (nm) | 255-430 | 400-800 | 2000-4500 |
| Resolution (nm) | 0.05-0.2 | 0.1-0.54 | 7.5-17 |
| Analog-to-digital conversion range | 12 bits | 12 bits | 12 bits |
| Eff. dynamic range (dB) | 63 | 63 | 45 |
| Diameter of aperture (mm) | 10 | 10 | 12 |
| Field of view (û) | 2 | 2 | 2 |

Figure 7:
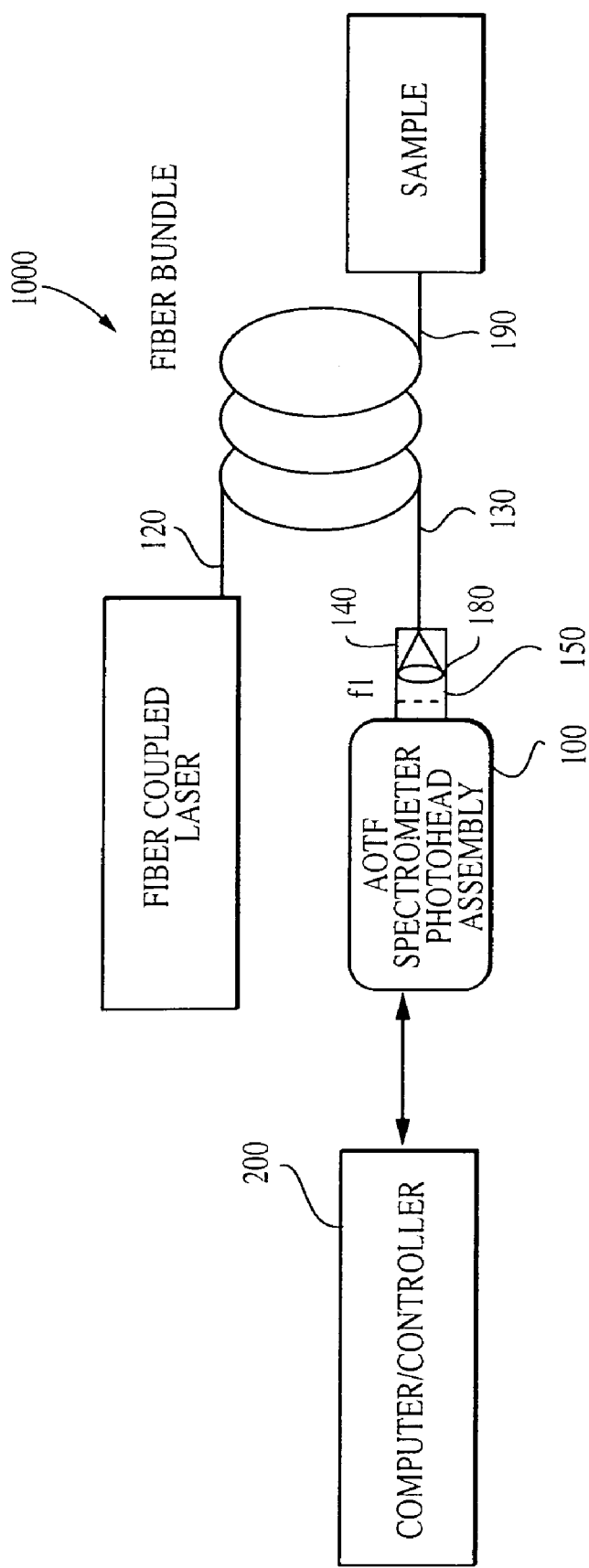
FIG. 7 shows in block diagram form an AO spectrometer system for use in fluorescence/Raman spectral measurement portable based system.

Portable AO Spectrometer Apparatus: FIG. 7 shows, in block form, the apparatus 1000 comprising a source of radiation (such as a laser source using either continuous wave or pulsed operation) using either AO spectrometer device 100A or 100B. Various spectroscopic applications include emission, absorption, fluorescence, and Raman spectral measurements. The preferred spectral range of observation for portable use is from 255 to 450 nm, which provides moderately high resolution when using the invention. The UV and visible-to-near-IR (Vis-NIR) instruments operate with no external cooling. The mid-IR AOS has a thermo-electrically cooled detector. Table 2 lists the specifications of a UV, Vis-NIR, and mid-IR type AOS based systems. FIG. 6a shows in block form, the optical and electronic relationship of the spectrometer apparatus 1000 using one of the AOS device embodiments.

The quartz AOS device preferably operates in two optical bands: UV to visible (255-430 nm) and visible to near-IR (400-800 nm). They can also be used for remote measurement of emission and absorption spectra to measure fluorescence and Raman spectra. The portable spectrometer has a 7.4 cm$^{-1}$ resolution, (similar to a conventional Fourier transform (FT) Raman spectrometer).

Figure 8:
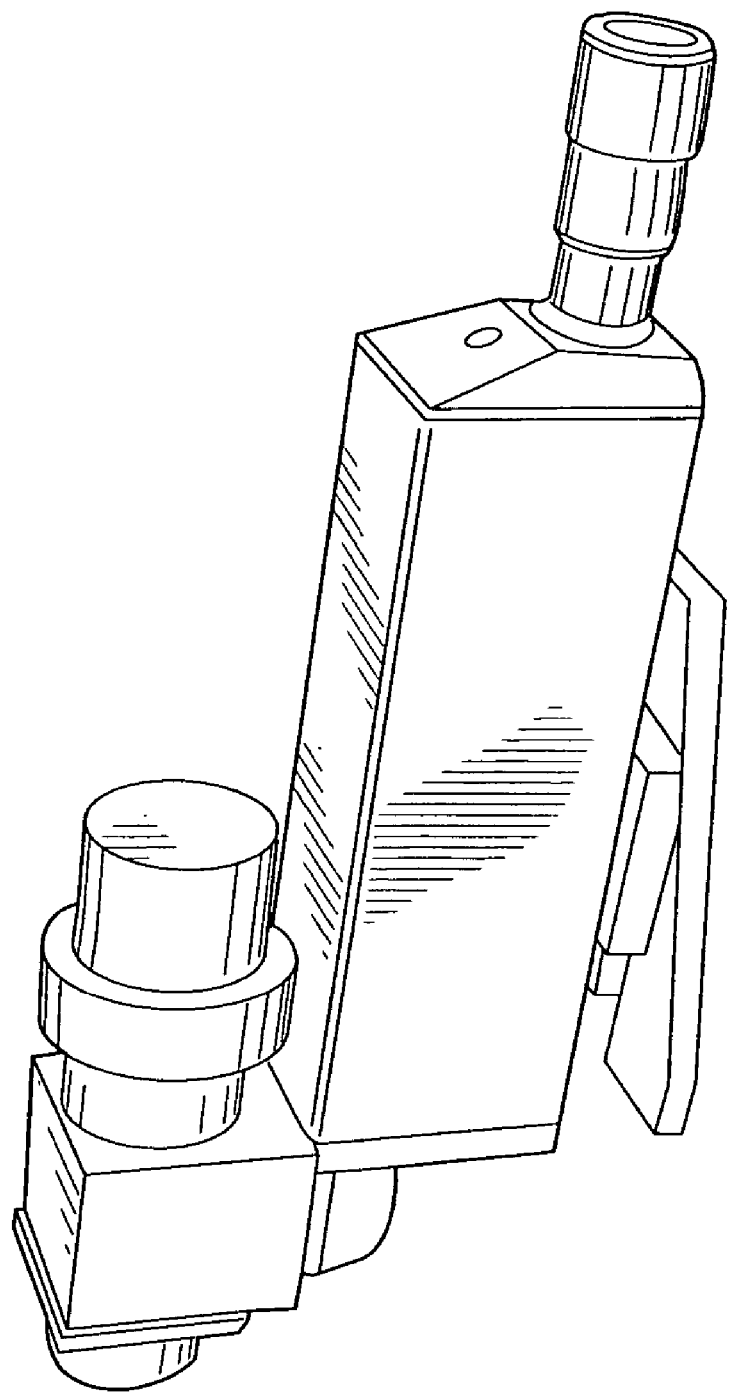
FIG. 8 shows a portable spectrometer system for performing Ramen and fluorescence type measurements.

As an example, a handheld spectrophotometer system, shown in FIGS. 7 and 8, comprise a compact fiber coupled laser in either a continuous wave or pulsed mode of operation, an acousto-optic tunable fitter (AOTF) based spectrometer using either AO crystal cell device embodiment discussed above, an optical fiber bundle wherein a multiple external receive fiber bundle surrounds a transmit fiber in the center, and a special annular attachment that attaches to the spectrometer that contains a fiber holder for aligning and securing the receive fiber bundle, a notch filter (rejection filter) at the laser wavelength if required, and a collimating lens that is positioned at the focal point away from the fiber holder.

The optical fiber located at the position to the output beam of the AOS 100 may be any suitable optic fiber such as quartz to use in the ultraviolet range, or zirconium fluoride, which is suitable for mid-infrared wavelengths. A sample cell may be coupled to the output beam of the optical fiber bundle, or directly coupled to the AOS 100. A sample cell contains a sample to be tested by the spectrometer apparatus. A lens in the attachment unit collimates the beam from the optical and transmits the desired observed radiation to the detector within the AOS 100. Alternately, a concave mirror at the opposite end of the sample cell can serve to refocus the beam into the return fiber. Note that some types of samples, such as solid samples, may not require a sample cell at all.

The laser wavelength of operation can be chosen based on the application. Most common laser wavelengths used are 266 nm and 532 nm. Large numerical aperture (i.e., 0.12) large core diameter (i.e., 200 microns) multimode is used in designing the fiber bundle. Optical fiber is selected that transmits light at these wavelengths. The fiber bundle consists of three legs. A single fiber forming a first leg can be connected to the laser using a simple SMA connector and carries light from the laser source to the sample being observed, a second leg of the optical fiber bundle consists of the fiber from the first leg as the center fiber and six fibers around it in a circle to collect the scattered light from the sample, and a third leg comprises at least six collection fibers that form a circle and are terminated with a SMA connector at the attachment device.

In a preferred exemplary form, a held-held Raman spectrophotometer includes an AO photo-head assembly 100 with a collinear quartz-type cell, a continuous wave 532-nm laser (140 mW power capability, frequency doubled Nd-YAG laser made by Brimrose, Inc.), a composite fiber bundle 130 (made by Fiber Guide), a holographic notch filter 150 at 532 nm (made by Kaiser). Light from the laser source coming through optical fiber leg 120 and joining a composite fiber bundle 190 that is directed and shined on a sample through the flexible hand-held optical fiber ending wherein scattered light from the sample is collected by the six or more collection fibers in a second leg that surrounds the leg 120 of the composite fiber 190. Reflected light from the sample is then transmitted to an annular focusing lens attachment 140 having a collimating quartz lens 180, a collimated beam passes through an optional notch filter 150 to the AOS photohead assembly 100. This portable hand-held optical fiber attachment device that can be readily detached from the optical device provides proper alignment, collimation and focusing action of a scattered beam from the sample to the optical instrument used. This annular attachment 180 can also be used with other types of spectrophotometers to provide portable field use for where alignment reliability is critical for use by non-experts using such instruments.

Operation of the AOS device 100 is controlled from the CPU that can control wavelength range, detection sensitivity and detected signal amplification. When scattered light passes through the notch filter 150, Rayleigh light is blocked and only light at greater wavelengths compared to the incident light enters the AOS device 100.

In detecting a fluorescence signal, either a UV laser source, or power of a visible laser can be increased whereby the florescence spectra can be displayed on a monitor. When a UV laser is chosen, the fibers and notch filter should be matched. For fluorescence measurements, a notch filter is not required since no loss of data occurs. If a pulsed laser source is used, detection of light should be done synchronously.

Portable Raman/Fluorescence Spectrometer: This is a preferred use of the invention as shown in actual packaged form in FIG. 8. This apparatus 1000 includes a laser source, either embodiment of the acousto-optic tunable filter based spectrometer devices 100A or 100B with matching optical components. When using a pulsed laser source, reflected light by an observed object scatters it. The scattered light is synchronously detected by the detector of the AOTF spectrometer photo-head assembly. For detection of Raman signals, a holographic notch filter is inserted in the optical telescope to block out the Rayleigh scattered light (such light has the same wavelength as the incident light). For use with fluorescence measurements, this filter is not required but it can be left inside the telescope since the spectral range covered that starts at wavelengths longer than the incident light. Either embodiment of the AO 100A or 100B can be used that use quartz crystal(s) for operation in wavelength ranges from UV to near IR. In general the field of view of a collinear AO crystal cell is relatively small and a matching optical telescope is required to intensify observed light from the sample. The telescope can be designed in such a way as to focus over a range of distance by electronically adjusting the zoom operation. Such a spectrometer covers a wide spectral range (260-430 nm, 400-800 nm).

Operation of spectrometer 1000 is similarly controlled by a computer. The laser controller electronics sends a synchronization pulse to the computer such that the detection of light is synchronized with the laser pulse. A zoom lens of the telescope can be electronically adjusted from the computer to get the best signal. The radio frequency generator and detector electronics can be located inside the computer tower.

The AO spectrometer system provides electronic tuning of the wavelength and requires no moving parts. The spectroscopic apparatus can be used to carry out both Raman and fluorescence measurements because the wavelength range covered by an AOS is much greater compared to a system based on using CCD camera and grating or other optical dispersive elements. Since either embodiment of the AO spectrometer device as discussed above can operate over much extensive wavelength range, the fluorescence spectra can also be determined using the same apparatus. The operational wavelength of the laser can be chosen based on the application. If a UV laser operating at 266 micrometers is used as the pulsed laser source, both strong Raman and fluorescence spectra are reflected from an observed sample depending upon the intensity of the laser pulse. The operation of the AO spectrometer device can be set in such a way as to select the appropriate wavelength range of measurement. The large spectral range of an AO spectrometer also is very useful for operation with a tunable laser source that could allow measurement of resonance Raman spectra that are in general a few orders of magnitude larger than the Raman spectra collected with non resonance wavelengths. Lasers operating at 532 nm can also provide Raman and fluorescence spectra but intensities are relatively smaller.

The held-held spectrometer apparatus 1000 can be mounted to a moving platform. Also, since the apparatus is small, light-weight and has optical fiber components for observing a sample in-situ, it can be used either in the field or room settings such as a medical office. Applications of the invention include monitoring of a patient for cancer, toxic agent monitoring in the environment, drug interdiction at airports and border crossings as part of law enforcement, airport security, spaceborne environmental monitoring, detection of forest fires, underwater monitoring of gases, diagnostics of engines using condition-based management of engine oil, and water quality monitoring.

Many modifications and variations of the present invention are possible in view of the above disclosure. Therefore to be understood, that within the scope of the appended claims, the to invention may be practiced otherwise than as specifically described.

What is claimed is:

1. An acousto-optical tunable filter (AOTF) device comprising birefringnent crystal cells in a non-collinear double AO crystal cell design, each cell has a transducer attached, the transducer in turn is configurably attached to a radio-frequency (RF) acoustic signal source to enable AO tunable filtering within each cell device at a desired tuned-frequency of operation, the transducers are positioned so as to provide an in-line single diffracted beam from un-polarized incident radiation coming through a combination two beam forming lenses, between the two crystal cells, an optical aperture member is attached to the cell device so as to let only collimated diffracted radiation pass through the first crystal and an un-diffracted beam is blocked by the optical aperture whereby this diffracted radiation with polarization normal to a given plane goes through a second diffraction when passing through the second AO crystal cell whose orientation is opposite of the first crystal, and the second crystal cell diffracts the radiation such that polarization of the doubly diffracted beam is normal to the given plane and perpendicular to a direction of radiation propagation and egress from the device.

2. The device according to claim 1, further comprising a second optical aperture that blocks the un-diffracted beam of the incident radiation from the second crystal wherein the diffracted radiation is then focused on a photodetector through a lens.

3. The device according to claim 1, wherein the AO-birefringnent crystal cells are made of quartz.

4. The device according to claim 1, wherein the AO-birefringnent crystal cells are made of $TeO_2$.

5. An acousto-optical tunable filter (AOTF) device comprising a birefringnent crystal cell in a shaped collinear AO crystal cell design, the cell has a transducer attached, the transducer in turn is configurably attached to a radio-frequency (RF) acoustic signal source to enable AO tunable filtering within each cell at a desired tuned-frequency of operation, the transducer is attached to the shaped collinear AO crystal cell having facets cut into the crystal cell such that unwanted sound waves are absorbed after traveling through an AO interaction region and the facets do not let sound waves get reflected into the crystal cell and retrace original paths in the AO interaction region, whereby diffraction of radiation occurs in the entire AO interaction region.

6. The device according to claim 5 that further comprises a polarizer that separates the diffracted beam that is subsequently transmitted and focused by a lens on a photodetector.

7. The device according to claim 5, wherein the AO-birefringnent crystal cell is made of quartz.

8. The device according to claim 5, wherein the AO-birefringnent crystal cell is made of $TeO_2$.

* * * * *